US008263551B2

(12) United States Patent
Olsen et al.

(10) Patent No.: US 8,263,551 B2
(45) Date of Patent: Sep. 11, 2012

(54) SOLUBLE, STABLE INSULIN-CONTAINING FORMULATIONS WITH A PROTAMINE SALT

(75) Inventors: Helle Birk Olsen, Allerod (DK); Niels Christian Kaarsholm, Vanlose (DK); Per Balschmidt, Espergaerde (DK)

(73) Assignee: Novo Nordisk A/S, Bagsvaerd (DK)

( * ) Notice: Subject to any disclaimer, the term of this patent is extended or adjusted under 35 U.S.C. 154(b) by 603 days.

(21) Appl. No.: 11/791,064

(22) PCT Filed: Nov. 21, 2005
(Under 37 CFR 1.47)

(86) PCT No.: PCT/EP2005/056105
§ 371 (c)(1),
(2), (4) Date: Oct. 8, 2008

(87) PCT Pub. No.: WO2006/053906
PCT Pub. Date: May 26, 2006

(65) Prior Publication Data
US 2011/0046049 A1 Feb. 24, 2011

Related U.S. Application Data

(60) Provisional application No. 60/631,556, filed on Nov. 29, 2004, provisional application No. 60/689,004, filed on Jun. 9, 2005.

(30) Foreign Application Priority Data

Nov. 22, 2004 (DK) .............................. PA 2004 01807
Jun. 8, 2005 (EP) ...................................... 05104998

(51) Int. Cl.
*A61K 38/17* (2006.01)
*A61K 38/28* (2006.01)
(52) U.S. Cl. ........... 514/6.6; 514/5.9; 514/6.4; 530/301; 530/304
(58) Field of Classification Search ........................ None
See application file for complete search history.

(56) References Cited

U.S. PATENT DOCUMENTS

| 5,474,978 | A | 12/1995 | Bakaysa et al. | |
|---|---|---|---|---|
| 5,747,642 | A | 5/1998 | DeFelippis | |
| 5,866,538 | A | 2/1999 | Norup et al. | |
| 5,948,751 | A * | 9/1999 | Kimer et al. | 514/6.3 |
| 6,174,856 | B1 | 1/2001 | Langballe et al. | |
| 6,211,144 | B1 * | 4/2001 | Havelund | 514/5.9 |
| 6,451,762 | B1 | 9/2002 | Havelund et al. | |
| 6,465,426 | B2 | 10/2002 | Brader | |
| 6,551,992 | B1 | 4/2003 | DeFelippis et al. | |

FOREIGN PATENT DOCUMENTS

| CA | 1339416 | 2/1988 |
|---|---|---|
| EP | 884053 | 12/1998 |
| GB | 2104382 | 3/1983 |
| JP | 63-179831 | 7/1988 |
| JP | 2002-504908 | 2/2002 |
| WO | WO 97/48413 | 12/1997 |
| WO | WO 98/56406 | 12/1998 |

OTHER PUBLICATIONS

Web entry for Protamine sulfate, accessed Mar. 23, 2011.*
Brange, J. et al., Diabetes Care, vol. 13(9), pp. 923-954 (1990).
Brange, J. et al., Acta Pharm Nord, vol. 4(4), pp. 149-158 (1992).
Brange, J. et al., Springer Verlag, pp. 17-73 (1987).
Brange, J. et al., Klu Acad Pub., pp. 17-46 (1994).
Heinemann, L. et al., Int. Symp., pp. 87-109 (1992).

* cited by examiner

*Primary Examiner* — Elly-Gerald Stoica
(74) *Attorney, Agent, or Firm* — Rosenmarie R. Wilk-Orescan

(57) ABSTRACT

The present invention relates to pharmaceutical formulations comprising insulin, an insulin analog, an insulin derivative, or a combination of any of the foregoing, and a salt of protamine, to methods of preparing such formulations, and to uses of such formulations in the treatment of diseases and conditions for which use of the insulin peptide(s) contained in such formulations is indicated. The present invention further relates to methods for increasing the stability and/or solubility of insulin in insulin-containing formulations at a pH less than 7.0 by adding a salt of protamine to the insulin-containing formulations.

18 Claims, 14 Drawing Sheets

SOLUBLE, STABLE INSULIN-CONTAINING FORMULATIONS WITH A PROTAMINE SALT

CROSS-REFERENCE TO RELATED APPLICATIONS

This application is a 35 U.S.C. §371 National Stage Application of International Patent Application PCT/EP2005/056105 (published as WO 2006/053906), filed Nov. 21, 2005, which claimed priority of Danish Patent Application PA 2004 01807, filed Nov. 22, 2004, and European Patent Application No. 05104998.9, filed Jun. 8, 2005; this application further claims priority under 35 U.S.C. §119 of U.S. Provisional Application Ser. Nos. 60/631,556 filed Nov. 29, 2004, and 60/689,004 filed Jun. 9, 2005.

FIELD OF THE INVENTION

The present invention relates to pharmaceutical formulations comprising insulin, an insulin analog, an insulin derivative, or a combination of any of the foregoing, and a salt of protamine, to methods of preparing such formulations, and to uses of such formulations in the treatment of diseases and conditions for which use of the insulin peptide(s) contained in such formulations is indicated. The present invention further relates to methods for increasing the stability and/or solubility of insulin in insulin-containing formulations at a pH less than 7.0 by adding a salt of protamine to the insulin-containing formulations.

BACKGROUND OF THE INVENTION

Diabetes mellitus is a metabolic disorder in which the ability to utilize glucose is more or less completely lost. About 2% of all people suffer from diabetes.

Since the discovery of insulin in the 1920's, continuous strides have been made to improve the treatment of diabetes mellitus. To help avoid extreme glucose levels, diabetic patients often practice insulin replacement therapy, whereby insulin is administered by injection.

In the treatment of diabetes mellitus, many varieties of insulin compositions have been suggested and used, including regular insulin, Semilente® insulin, isophane insulin, insulin zinc suspensions, protamine zinc insulin, and Ultralente® insulin. As diabetic patients typically are treated with insulin for several decades, there is a major need for safe and life quality improving insulin compositions. Some of the commercially available insulin compositions are characterized by a fast onset of action, while other compositions have a relatively slow onset but show a more or less prolonged action. Fast acting insulin compositions are usually solutions of insulin, while retarded acting insulin compositions can be suspensions containing insulin in crystalline and/or amorphous form precipitated by addition of zinc salts alone or by addition of protamine or by a combination of both. In addition, some patients use compositions having both a fast onset of action and a more prolonged action. Such a composition may be an insulin solution wherein protamine insulin crystals are suspended. Some patients prepare the final composition themselves by mixing an insulin solution with a suspension composition in the desired ratio.

Human insulin consists of two polypeptide chains, the so-called A and B chains, which contain 21 and 30 amino acid residues, respectively. The A and B chains are interconnected by two cystine disulphide bridges and a third disulfide bridge is intra A chain. Insulin from most other species has a similar construction, but may not contain the same amino acid residues at corresponding positions.

The development of genetic engineering has made it possible to easily prepare a great variety of insulin compounds analogous to human insulin. In these insulin analogs, one or more of the amino acid residues have been substituted with other amino acid residues which can be coded for by the nucleotide sequences. Since human insulin, as explained above, contains 51 amino acid residues, it is obvious that a large number of insulin analogs is possible, and a great variety of analogs with interesting properties have been prepared. In human insulin solutions with a concentration of interest for injectable compositions, the insulin molecule is present in associated form as a hexamer (Brange et al. *Diabetes Care* 13, (1990), 923-954). After subcutaneous injection, it is believed that the rate of absorption by the blood stream is dependent on the size of the molecule, and it has been found that insulin analogues with amino acid residue substitutions which counteract or inhibit this hexamer formation have an unusually fast onset of action (Brange et al.: Ibid). This can be of great therapeutic value for the diabetic patient.

A general survey of pharmaceutical compositions containing insulin is given by Brange et al. in Galenics of Insulin, Springer-Verlag (Berlin, 1987). Scott and Fisher (1936) disclose suspensions of insulin containing 1 mM protamine sulphate and 0.15 mM insulin at pH 7.2.

Pharmaceutical compositions which are based on analogues of human insulin have e.g. been presented by Heinemann et al., Lutterman et al. and Wiefels et al. at the "Frontiers in Insulin Pharmacology" International Symposium in Hamburg, 1992.

U.S. Pat. No. 5,474,978 (Eli Lilly) discloses a rapidly acting parenteral formulation comprising a human insulin analogue hexamer complex consisting of six monomeric insulin analogues, zinc ions and at least three molecules of a phenolic derivative.

Normally, insulin compositions are administered by subcutaneous injection. What is important for the patient is the profile of action of the insulin composition, i.e. the action of insulin on the glucose metabolism as a function of the time from the injection, including the time for the onset of insulin action, the maximum value and the total duration of action. A variety of insulin compositions with different profiles of action are required by patients. An individual patient may thus on the same day use insulin compositions with very different profiles of action. The profile of action required for any given patient at any given time depends upon several factors, e.g. the time of the day and the amount and composition of any meal eaten by the patient.

Also important for the patient is the chemical stability of the insulin compositions, especially due to the abundant use of pen-like injection devices such as devices which contain Penfill® cartridges, in which an insulin composition is stored until the entire cartridge is empty. This may last 1 to 2 weeks or more for devices containing a 1.5 or 3.0 ml cartridge. During storage, covalent chemical changes in the insulin structure occur. This may lead to the formation of molecules which are less active and potentially immunogenic such as deamidation products and higher molecular weight transformation products (dimers, polymers, etc.). A comprehensive study on the chemical stability of insulin is given by Jens Brange in "Stability of Insulin", Kluwer Academic Publishers, 1994.

Compositions comprising insulin and insulin analogues are traditionally formulated using various additives, for example sodium phosphate (buffer), $Zn^{2+}$ (stabilizer), phenol/m-cresol (preservative and stabilizer), sodium chloride (isotonicity agent and stabilizer), and glycerol/mannitol (isotonicity agents).

The shelf-life of insulin products is mainly compromised by the formation of soluble aggregates (dimers and polymers) over time, despite the fact that insulin is typically stored at a low temperature of no more than about 5° C., which improves the shelf-life considerably compared to storage e.g. at room temperature. In addition, insulin products are subject to the formation of insoluble aggregates (fibrils) as a result of shaking, e.g. when carried in the pocket of a patient or during transport. It is essential for the quality of an insulin product that the tendency to form such soluble and insoluble aggregates as a result of chemical or physical influences is reduced to an absolute minimum.

*Acta Pharmaceutica Nordica* 4(4), 1992, pp. 149-158 discloses insulin compositions with a sodium chloride concentration in the range of 0 to 250 mM. The major part of the compositions, including those which additionally comprise glycerol, contain a rather high amount of sodium chloride, i.e. 0.7%, corresponding approximately to a concentration of 120 mM.

U.S. Pat. No. 5,866,538 (Novo Nordisk) discloses insulin compositions having improved chemical stability, the compositions comprising human insulin or an analog or derivative thereof, glycerol and/or mannitol and 5-100 mM of a halogenide, e.g. sodium chloride.

U.S. Pat. No. 6,174,856 (Novo Nordisk) discloses stabilized aqueous compositions comprising human insulin or an analog or derivative thereof, a buffer selected from glycylglycine, citrate or TRIS and metal ions, in particular, calcium or magnesium ions.

U.S. Pat. No. 6,451,762 (Novo Nordisk) discloses protracted acting water soluble aggregates of derivatives of human insulin.

U.S. Pat. No. 6,551,992 (Eli Lilly) discloses monomeric insulin analog formulations stabilized against aggregation in which the buffering agent is either TRIS or arginine.

U.S. Pat. No. 5,747,642 (Eli Lilly) discloses parenteral pharmaceutical formulations which comprise a monomeric insulin analog, zinc, protamine and a phenolic derivative.

U.S. Pat. No. 6,465,426 (Eli Lilly) discloses insoluble compositions comprising an acylated insulin or acyalted insulin analog complexed with zinc, protamine and a phenolic compound such that the resulting microcrystal is analogous to the neutral protamine Hagedorn (NPH) insulin crystal form.

Although progress has been made in the chemical and physical stabilization of insulin-containing compositions, the need still remains for soluble, stable formulations of insulin or analogs or derivatives thereof, or mixtures of the foregoing, that exhibit a prolonged action profile upon administration in vivo.

SUMMARY OF THE INVENTION

The present application discloses that formulations containing certain salts of protamine at certain concentrations allow soluble stable preparations of insulin, insulin analogs, insulin derivatives or mixtures of the foregoing to be formulated at pHs below 7.0. The present formulations are also physically and chemically stable at a pH below 7.0 and exhibit a prolonged profile of action thus rendering them shelf-stable and suitable for invasive (e.g. injection, subcutaneous injection, intramuscular, intraveneous or infusion) as well as non-invasive (e.g. nasal, oral, pulmonary, transdermal or transmucosal e.g. buccal) means of administration.

The present invention therefore relates to pharmaceutical formulations comprising insulin, insulin analogs, insulin derivatives or mixtures of the foregoing, and a salt of protamine where the protamine salt is present in a concentration of at least 0.25 mM and the pH of the formulation is less than about 7.0. The pharmaceutical formulations of the invention may further contain at least one of the following components: a preservative, a divalent metal ion such as zinc cobalt, magnesium or calcium or combinations of these ions, an isotonicity agent, a buffer and a surfactant.

The present invention further relates to methods of treatment using the pharmaceutical formulations of the invention where the compositions are administered in an amount effective to combat the disease, condition, or disorder for which administration of the insulin peptide contained in the formulation is indicated. In one embodiment, the formulations of the invention may be used in the treatment of type 1 and type 2 diabetes.

In addition the present invention also relates to a method for increasing the physical and chemical stability of an insulin-containing formulation, where the method comprises adding protamine salt at a concentration of at least 0.25 mM.

The present invention also relates to methods for producing the pharmaceutical formutations of the invention.

In one embodiment, the method for preparing formulations of the invention comprises:
a) preparing a solution by dissolving a divalent metal ion in water or buffer;
b) preparing a solution by dissolving the preservative in water or buffer;
c) preparing a solution by dissolving the isotonicity agent in water or buffer;
d) preparing a solution by dissolving the surfactant in water or buffer;
e) preparing a solution by dissolving the insulin, insulin analog, insulin derivative or a mixture of the foregoing in water or buffer;
f) preparing a solution by dissolving a protamine salt in buffer or water;
g) mixing solution e) and one or more of solutions a), b), c), and d);
h) mixing solution g) with solution f); and
i) adjusting the pH of the mixture in h); to the desired pH of less than 7.0.

BRIEF DESCRIPTION OF THE FIGURES

FIG. 2A shows the pH-dependence of human insulin preparations containing 0.6 mM human insulin, 0.3 mM Zn2+, 30 mM phenol, 1.6% glycerol and either 0.7 mM protamine-sulphate or 0.7, 1.2, 1.6 or 2.0 mM protamine-acetate;

FIG. 2B shows the pH-dependence of human insulin preparations containing 0.6 mM human insulin, 30 mM phenol, 1.6% glycerol, 1.2 mM protamine-acetate, and 0.3, 0.4 or 0.6 mM Zn2+; and FIG. 2C shows the pH-dependence of preparations of 0.6 mM human insulin, 30 mM phenol, 1.6% glycerol, 2.0 mM protamine-acetate, and 0.0, 0.2, 0.4 and 0.6 mM Zn2+.

DESCRIPTION OF THE INVENTION

The pharmaceutical formulations of the invention comprise insulin and a salt of protamine where the protamine salt is present in a concentration of at least 0.25 mM and the pH of the formulation is less than about 7.0.

The pharmaceutical formulations of the invention are chemically stable and soluble at pHs less than 7.0. By "soluble at a given pH" is meant that the insulin contained in the formulation of the invention is fully dissolved at the pH of the formulation where methods for determining whether the insulin contained in the formulation of the invention is dissolved are known in the art.

In one embodiment, the pharmaceutical formulation may be subjected to centrifugation for 20 minutes at 30,000 g and then the insulin concentration in the supernatant may be determined by RP-HPLC. If this concentration is equal within experimental error to the insulin concentration originally used to make the formulation, then the insulin is fully soluble in the formulation of the invention.

In another embodiment, the solubility of the insulin peptide (s) in a formulation of the invention can simply be determined by examining by eye the container in which the formulation is contained. Insulin is soluble if the solution is clear to the eye and no particulate matter is either suspended or precipitated on the sides/bottom of the container.

Figure 13:
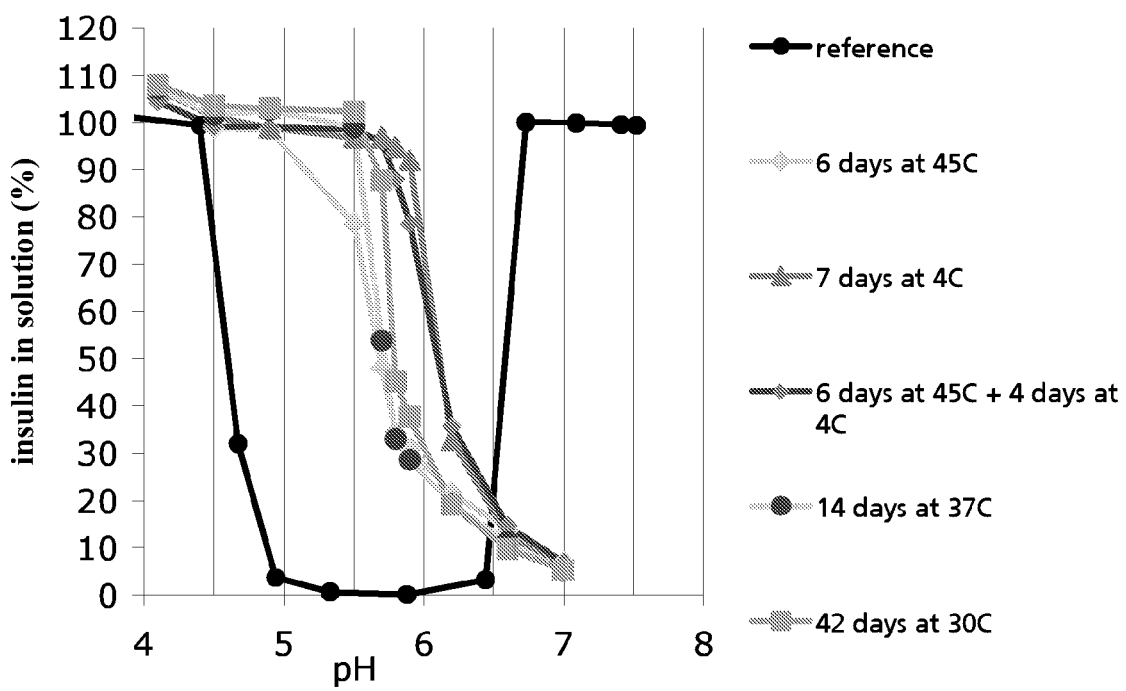
FIG. 13 shows the solubility of insulin vs. pH in a preparation of 0.6 mM human insulin, 1.6 mM protamine acetate, 60 mM phenol, 1.6% glycerol after storage at temperatures and times as indicated in the Figure. "Reference" is 0.6 mM human insulin, 0.3 mM Zn2+, 30 mM phenol, 1.6% glycerol stored at room temperature for 4 days.
Figure 14:
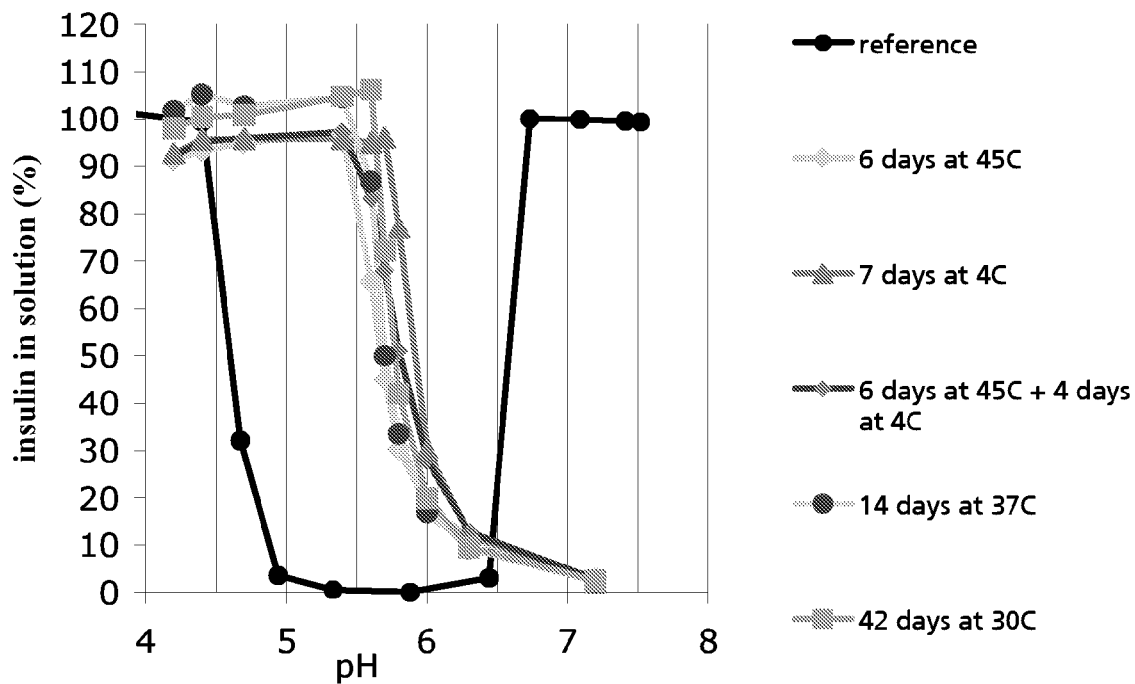
FIG. 14 shows the solubility of insulin vs. pH in a preparation of 2.0 mM human insulin, 4.0 mM protamine acetate, 60 mM phenol, 1.6% glycerol after storage at temperatures and time intervals as indicated in the Figure. "Reference" is 0.6 mM human insulin, 0.3 mM Zn2+, 30 mM phenol, 1.6% glycerol stored at room temperature for 4 days.
Figure 15:
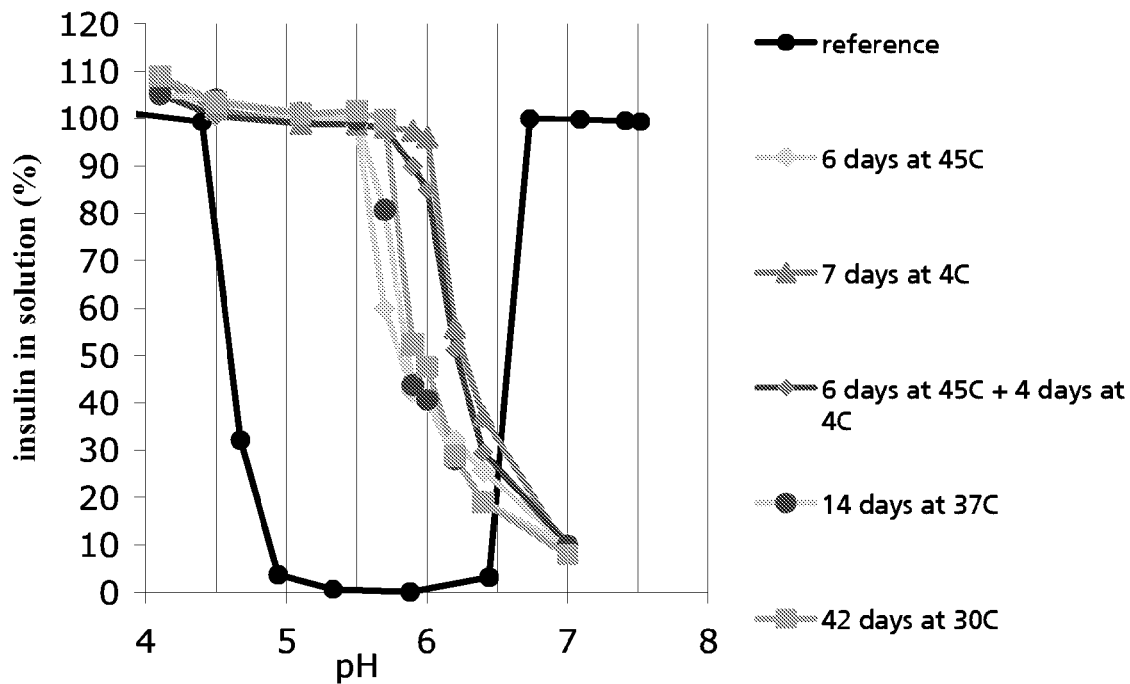
FIG. 15 shows the solubility of insulin vs. pH in a preparation of 0.6 mM human insulin, 2.0 mM protamine acetate, 40 mM phenol, 1.6% glycerol after storage at temperatures and time intervals as indicated in the Figure. "Reference" is 0.6 mM human insulin, 0.3 mM Zn2+, 30 mM phenol, 1.6% glycerol stored at room temperature for 4 days.
Figure 16:
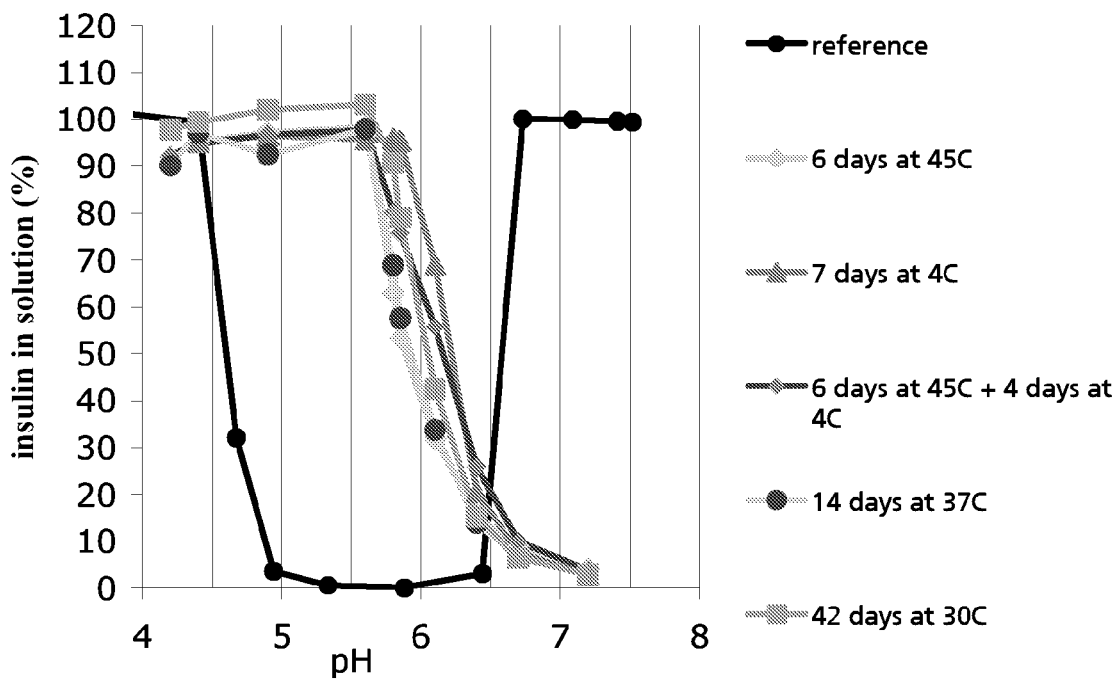
FIG. 16 shows the solubility of insulin vs. pH in a preparation of 2.0 mM human insulin, 4.0 mM protamine acetate, 25 mM m-cresol, 1.6% glycerol after storage at temperatures and time intervals as indicated in the Figure. "Reference" is 0.6 mM human insulin, 0.3 mM Zn2+, 30 mM phenol, 1.6% glycerol stored at room temperature for 4 days.
Figure 17:
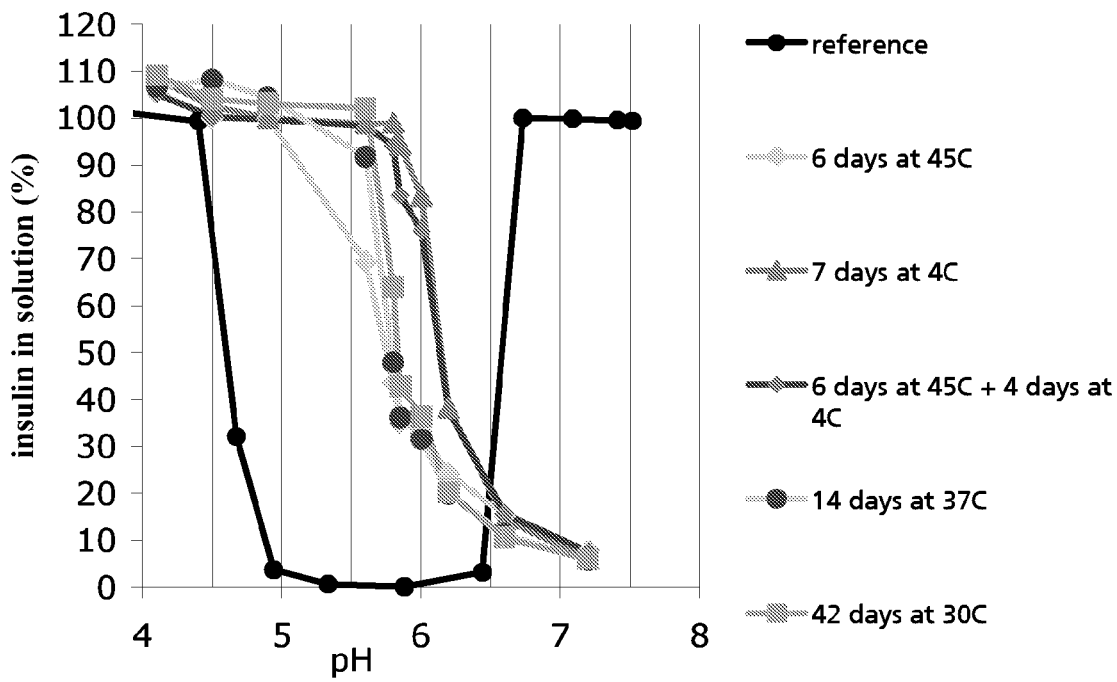
FIG. 17 shows the solubility of insulin vs. pH in a preparation of 0.6 mM human insulin, 2.0 mM protamine acetate, 60 mM phenol, 1.6% glycerol after storage at temperatures and time intervals as stated in the legends. Reference is 0.6 mM human insulin, 0.3 mM Zn2+, 30 mM phenol, 1.6% glycerol stored at room temperature for 4 days.

Of course, it is to be understood by the skilled artisan that the solubility of insulin in a formulation of the invention may be affected not only by the composition of the formulation and its pH but also by the temperature and time at which the formulation is stored prior to measurement of solubility (see Example 6). For example, while storage of the formulations of the invention at a temperature of 45° C. may narrow the range of pH values where solubility is observed, any precipitation of insulin from the formulations of the invention observed at 45° C. may be reversed by lowering the temperature of the formulation (see, for example, FIGS. 13 and 15). Thus, for example, if a formulation is a clear solution (i.e. soluble) at 4° C. at a given pH between pH 5-6 but starts to precipitate when stored at 45° C., this precipitate will be resolvated when the formulation is stored at 4° C. afterwards.

In the formulations of the invention, the insulin to be included may be selected from insulin, where "insulin" is understood to mean human insulin, [where "human insulin" means insulin having the amino acid sequence shown in DSHW Nicol and L F Smith: *Nature*, (1960) 4736:483-485, which is hereby incorporated by reference], human insulin analogs, human insulin derivatives or mixtures thereof.

In one embodiment the insulin is human insulin.

In another embodiment the insulin is an analogue of human insulin.

In another embodiment the insulin is a derivative of human insulin.

In another embodiment the insulin is an analogue of human insulin wherein position B28 is Asp, Glu, Lys, Leu, Val, or Ala.

In another embodiment the insulin is an analogue of human insulin wherein position B28 is Asp, Glu or Lys.

In another embodiment the insulin is an analogue of human insulin wherein position B28 is Asp or Glu.

In another embodiment the insulin is an analogue of human insulin wherein position B28 is Asp.

In another embodiment the insulin is an analogue of human insulin wherein position B28 is Glu.

In another embodiment the insulin is an analogue of human insulin wherein position B29 is Pro, Asp or Glu.

In another embodiment the insulin is an analogue of human insulin wherein position B29 is Pro or Glu.

In another embodiment the insulin is an analogue of human insulin wherein position B29 is Pro.

In another embodiment the insulin is an analogue of human insulin wherein position B29 is Glu.

In another embodiment the insulin is an analogue of human insulin wherein position B28 is Asp or Lys, and position B29 is Lys or Pro.

In another embodiment the insulin is an analogue of human insulin wherein position B9 is Asp or Glu.

In another embodiment the insulin is an analogue of human insulin wherein position B10 is Asp or Glu or Gln.

In another embodiment the insulin is an analogue of human insulin wherein position B10 is Glu.

In another embodiment the insulin is an analogue of human insulin wherein position B10 is Gln.

In another embodiment the insulin is an analogue of human insulin wherein position B1 is Gly.

In another embodiment the insulin is an analogue of human insulin wherein position B3 is Lys, Thr, Ser, Ala or Gln.

In another embodiment the insulin is an analogue of human insulin wherein position B3 is Lys, Thr, Ser or Ala.

In another embodiment the insulin is an analogue of human insulin wherein position B3 is Lys or Ala.

In another embodiment the insulin is an analogue of human insulin wherein position B3 is Lys.

In another embodiment the insulin is an analogue of human insulin wherein position B3 is Lys and position B29 is Glu.

In another embodiment the insulin is an analogue of human insulin wherein position B25 is deleted.

In another embodiment the insulin is an analogue of human insulin wherein position B27 is deleted.

In another embodiment the insulin is an analogue of human insulin wherein position B30 is deleted.

In another embodiment the insulin is an analogue of human insulin wherein position A18 is Gln.

In another embodiment the insulin is an analogue of human insulin wherein position A21 is Ala, Arg, Gln, Glu, Gly, His, Ile, Leu, Met, Phe, Ser, Thr, Trp, Tyr, Val or hSer.

In another embodiment the insulin is an analogue of human insulin wherein position A21 is Ala, Arg, Gln, Gly, Ile, Leu, Phe, Ser, Thr, Val or hSer.

In another embodiment the insulin is an analogue of human insulin wherein position A21 is Ala or Gly.

In another embodiment the insulin is an analogue of human insulin wherein position A21 is Gly.

In another embodiment the insulin is a derivative of human insulin or an analogue thereof having one or more lipophilic substituents.

In another embodiment the insulin is a derivative of human insulin or an analogue thereof wherein the $N^\epsilon$-amino group in position B29Lys is modified by covalent acylation with a hydrophobic moiety such as a fatty acid derivative or an litocholic acid derivative.

In another embodiment the insulin derivative is selected from the group consisting of B29$N^\epsilon$-hexadecandioyl-γ-Glu desB30 insulin, B29-N$^\epsilon$-myristoyl-des(B30) human insulin, B29-N$^\epsilon$-palmitoyl-des(B30) human insulin, B29-N$^\epsilon$-myristoyl human insulin, B29-N$^\epsilon$-palmitoyl human insulin, B28-N$^\epsilon$-myristoyl Lys$^{B28}$ Pro$^{B29}$ human insulin, B28-N$^\epsilon$-palmitoyl Lys$^{B28}$ Pro$^{B29}$ human insulin, B30-N$^\epsilon$-myristoyl-Thr$^{B29A}$S$^{B30}$ human insulin, B30-N$^\epsilon$-palmitoyl-Thr$^{B29}$Lys$^{B30}$ human insulin, B29-N$^\epsilon$-(N-palmitoyl-γ-glutamyl)-des(B30) human insulin, B29-N$^\epsilon$-(N-litho-cholyl-γ-glutamyl)-des(B30) human insulin, B29-N$^\epsilon$-(ω-carboxyheptadecanoyl)-des(B30) human insulin and B29-N$^\epsilon$-(ω-carboxyheptadecanoyl) human insulin.

In another embodiment, the analogs of human insulin contain any combination of additional stabilizing substitutions.

In another embodiment, the analogs of human insulin contain any combination of the additional stabilizing substitutions in positions B1, B3, A18 and A21.

In another embodiment the insulin is an analogue of human insulin selected from the group consisting of:
B28D
B25H
desB27
B28K, B29P
B3K, B29E
B29E
desB25
B9E/D
B10E/D/Q.

In another embodiment the insulin is an analogue of human insulin selected from the group consisting of:
A21G
A21Q,
A21A,
A21T
A21R All of the combinations below could be A21Q/A/T/R as well:
A21G, B28K, B29P
A21G, B28D
A21G, B28E
A21G, B3K, B29E
A21G, desB27
A21G, B9E
A21G, B9D
A21G, B10E
A21G, desB25
A21G, B25H
A21G, desB30
A21G, B28K, B29P
A21G, B28K, B29P, desB30
A21G, B28D, desB30
A21G, B28E
A21G, B28E, desB30
A21G, B3K, B29E
A21G, B3K, B29E, desB30
A21G, desB27, desB30
A21G, B9E/D
A21G, B9E, desB30
A21G, B9D, desB30
A21G, B10E/D/Q
A21G, B10E, desB30
A21G, B10Q, desB30
A21G, desB25, desB30.

In another embodiment the insulin is an analogue of human insulin selected from the group consisting of:
B1G, A21G
B1G, A21G, B28K, B29P
B1G, A21G, B28D
B1G, A21G, B28E
B1G, A21G, B3K, B29E
B1G, A21G, desB27
B1G, A21G, B9E
B1G, A21G, B9D
B1G, A21G, B10E
B1G, A21G, B10Q
B1G, A21G, desB25
B1G, A21G, B25H
B1G, A21G, desB30
B1G, A21G, B28K, B29P
B1G, A21G, B28K, B29P, desB30
B1G, A21G, B28D, desB30
B1G, A21G, B28E
B1G, A21G, B28E, desB30
B1G, A21G, B3K, B29E
B1G, A21G, B3K, B29E, desB30
B1G, A21G, desB27, desB30
B1G, A21G, B9E/D
B1G, A21G, B9E, desB30
B1G, A21G, B9D, desB30
B1G, A21G, B10E/D/Q
B1G, A21G, B10E, desB30
B1G, A21G, B10Q, desB30
B1G, A21G, desB25, desB30,
B1G, A21G, B25H, desB30

In another embodiment, the insulin is an analogue of human insulin from above three lists further modified in positions B3 and A18, eg B3T, B3S, B3Q and A18Q.

In another embodiment, the insulin is an analogue of human insulin from the above three lists further modified as follows:
B3T, B28D
B3T, desB27.

In another embodiment, the insulin is an analogue of human insulin from the above three lists further modified by deletion of B30.

In another embodiment, the insulin analogs and derivatives are selected from among those disclosed in EP 0 792 290 (Novo Nordisk A/S), EP 0 214 826 and EP 0 705 275 (Novo Nordisk NS), U.S. Pat. No. 5,504,188 (Eli Lilly), EP 0 368 187 (Aventis), U.S. Pat. Nos. 5,750,497 and 6,011,007, EP 375437 and EP 383472 and where such insulins may include, but are not limited to, Lys$^{B29}$ (N$^\epsilon$-tetradecanoyl) des(B30) human insulin, Lys$^{B29}$-(N$^\epsilon$-(γ-glutamyl-N$^\alpha$-lithocholyl) des(B30) human insulin, N$^{\epsilon B29}$-octanoyl insulin, insulin glargine (insulin glargine, also known as Lantus®, differs from human insulin in that the amino acid asparagine at position A21 is replaced by glycine and two arginines are added to the C-terminus of the B-chain), insulin glulisine (insulin glulisine, also known as Apidra®, differs from human insulin in that the amino acid asparagine at position B3 is replaced by lysine and the lysine in position B29 is replaced by glutamic acid) Lys$^{B28}$ Pro$^{B29}$ human insulin (Humalog®), Asp$^{B28}$ human insulin, or insulin aspart (Novolog®).

In one embodiment, the insulin is a derivative of human insulin or a human insulin analogue where the derivative contains at least one lysine residue and a lipophilic substituent is attached to the epsilon amino group of the lysine residue.

In one embodiment, the lysine residue to which the lipophilic substituent is attached is present at position B28 of the insulin peptide.

In another embodiment, the lysine residue to which the lipophilic substituent is attached is present at position B29 of the insulin peptide.

In yet another embodiment, lipophilic substituent is an acyl group corresponding to a carboxylic acid having at least 6 carbon atoms.

In another embodiment, the lipophilic substituent is an acyl group, branched or unbranched, which corresponds to a carboxylic acid having a chain of carbon atoms 8 to 24 atoms long.

In another embodiment, the lipophilic substituent is an acyl group corresponding to a fatty acid having at least 6 carbon atoms.

In another embodiment, the lipophilic substituent is an acyl group corresponding to a linear, saturated carboxylic acid having from 6 to 24 carbon atoms.

In another embodiment, the lipophilic substituent is an acyl group corresponding to a linear, saturated carboxylic acid having from 8 to 12 carbon atoms.

In another embodiment, the lipophilic substituent is an acyl group corresponding to a linear, saturated carboxylic acid having from 10 to 16 carbon atoms.

In another embodiment, the lipophilic substituent is an oligo oxyethylene group comprising up to 10, preferably up to 5, oxyethylene units.

In another embodiment, the lipophilic substituent is an oligo oxypropylene group comprising up to 10, preferably up to 5, oxypropylene units.

In one preferred embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys; Phe$^{B1}$ may be deleted; the epsilon-amino group of Lys$^{B29}$ has a lipophilic substituent which comprises at least 6 carbon atoms; and 2-4 Zn$^{2+}$ ions may be bound to each insulin hexamer with the proviso that when B30 is Thr or Ala and A21 and B3 are both Asn, and Phe$^{B1}$ is not deleted, then 2-4 Zn$^{2+}$ ions are bound to each hexamer of the insulin derivative.

In another embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys, with the proviso that if the B30 amino acid residue is Ala or Thr, then at least one of the residues A21 and B3 is different from Asn; Phe$^{B1}$ may be deleted; and the epsilon-amino group of Lys$^{B29}$ has a lipophilic substituent which comprises at least 6 carbon atoms.

In another embodiment, the invention relates to a human insulin derivative in which the B30 amino acid residue is deleted or is any amino acid residue which can be coded for by the genetic code except Lys, Arg and Cys; the A21 and the B3 amino acid residues are, independently, any amino acid residues which can be coded for by the genetic code except Lys, Arg and Cys; Phe$^{B1}$ may be deleted; the epsilon-amino group of Lys$^{B29}$ has a lipophilic substituent which comprises at least 6 carbon atoms; and 2-4 Zn$^{2+}$ ions are bound to each insulin hexamer.

In one embodiment, the formulations of the invention contain insulin in a concentration from about 0.25 mM to about 5.0 mM.

In another embodiment, the formulations of the invention contain insulin in a concentration from about 0.25 mM to about 4.0 mM.

In yet another embodiment, the formulations of the invention contain insulin in a concentration from about 0.25 mM to about 3.0 mM.

In yet another embodiment, the formulations of the invention contain insulin in a concentration from about 0.3 mM to about 1.5 mM.

In yet another embodiment, the formulations of the invention contain insulin in a concentration from 0.4 mM, from 0.8 mM or from 1.3 mM.

In the formulations of the invention, the protamine salt to be included is to be a protamine salt other than protamine sulphate where such salts include, but are not limited to, acetate, bromide, chloride, caproate, trifluoroacetate, HCO$_3$, propionate, lactate, formiate, nitrate, citrate, monohydrogenphosphate, dihydrogenphosphate, tartrate, or perchlorate salts of protamine or mixtures of any two protamine salts. "Protamine" as used herein refers to the generic name of a group of strongly basic proteins present in sperm cells in salt-like combination with nucleic acids. Normally, protamines to be used together with insulin are obtained from e.g. salmon (salmine), rainbow trout (iridine), herring (clupeine), sturgeon (sturine), or spanish mackerel or tuna (thynnine) and a wide variety of salts of protamines are commercially available. Of course, it is understood that the peptide composition of a specific protamine may vary depending of which family, genera or species of fish it is obtained from. Protamine usually contains four major components, i.e. single-chain peptides containing about 30-32 residues of which about 21-22 are arginines. The N-terminal is proline for each of the four main components, and since no other amino groups are present in the sequence, chemical modification of protamine by a particular salt is expected to be homogenous in this context.

In one embodiment, the protamine salts used in the present invention are from salmon.

In another embodiment, the protamine salts used in the present invention are from herring.

In another embodiment, the protamine salts used in the present invention are from rainbow trout.

In another embodiment, the protamine salts used in the present invention are from tuna.

In another embodiment, the protamine salt is selected from the group consisting of propionate, lactate, formiate, nitrate, acetate, citrate, caproate, monohydrogenphosphate, dihydrogenphosphate salts of protamine.

In another embodiment, the protamine salt is selected from the group consisting of propionate, lactate, formiate, nitrate and acetate salts of protamine.

In another embodiment, the protamine salt is selected from acetate salts of protamine.

In a further embodiment, when the protamine salt to be included in the formulation of the invention is to be a mixture of two different salts, one salt will be acetate and the other salt is selected from the group consisting of propionate, lactate, formiate, and nitrate salts of protamine. It is to be understood that when the protamine salt to be included in the formulation of the invention is to be a mixture of two different salts, the molar ratio between the two different salts may be from 0.1:1 to 1:1.

In one embodiment, the molar ratio of protamine salt to insulin in the formulations of the invention is from about 0.5 to about 100.

In another embodiment, the molar ratio of protamine salt to insulin in the formulations of the invention is from about 0.5 to about 10.

In another embodiment, the molar ratio of protamine salt to insulin in the formulations of the invention is from about 0.5 to 5.

In another embodiment, the molar ratio of protamine salt to insulin in the formulations of the invention is from about 1 to 3.

In another embodiment of the invention, the formulation has a pH less than about 7.0 where the term "about" as used in connection with pH means + or −0.1 pH units from the stated number.

In a further embodiment of the invention, the formulation has a pH in the range from about 4.0 to about 6.5.

In yet a further embodiment of the invention, the formulation has a pH in the range from about 4.5 to about 6.0.

In yet a further embodiment of the invention, the formulation has a pH in the range from about 5.0 to about 6.0.

In yet a further embodiment of the invention, the formulation has a pH in the range from about 5.0 to about 5.6.

It has been observed that the pH of the formulations of the invention is quite stable in that only very minor pH-migrations in the formulations of the invention have been observed to occur over time (data not shown) and that these variations are typically the pH-meter to pH-meter variations that are normally observed in measuring the pH of formulations.

In another embodiment of the invention, the formulations contain, in addition to an insulin and a protamine salt, at least one of the following components: a preservative, a divalent metal ion such as zinc, and an isotonicity agent.

In another embodiment of the invention, the formulations contain, in addition to an insulin and a protamine salt, at least two of the following components: a preservative, a divalent metal ion such as zinc, and an isotonicity agent.

In another embodiment of the invention, the formulations contain, in addition to an insulin and a protamine salt, all three of the following components: a preservative, a divalent metal ion such as zinc, and an isotonicity agent.

In another embodiment of the invention, the formulation contains no divalent metal ion.

Where a pharmaceutically acceptable preservative is to be included in the formulations of the invention, the preservative is selected from the group consisting of phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. Each one of these specific preservatives constitutes an alternative embodiment of the invention. In a preferred embodiment of the invention the preservative is phenol or m-cresol. In another preferred embodiment of the invention the preservative is phenol. In another preferred embodiment of the invention the preservative is m-cresol.

In a further embodiment of the invention the preservative is present in a concentration from about 0.1 mg/ml to about 50 mg/ml, more preferably in a concentration from about 0.1 mg/ml to about 25 mg/ml, and most preferably in a concentration from about 0.1 mg/ml to about 10 mg/ml.

The use of a preservative in pharmaceutical compositions is well-known to the skilled person. For convenience reference is made to Remington: *The Science and Practice of Pharmacy*, 19$^{th}$ edition, 1995.

Where a divalent metal ion is to be included in the formulations of the invention, the divalent metal ion may be calcium, magnesium or zinc or a combination thereof.

In one embodiment, the divalent metal ion is zinc.

In another embodiment, the concentration of zinc in the formulations of the invention is less than a molar ratio of 3 $ZN^{2+}$ per insulin.

In another embodiment, the concentration of zinc in the formulations of the invention is less than a molar ratio of 2 $ZN^{2+}$ per insulin.

In another embodiment, the concentration of zinc in the formulations of the invention is less than a molar ratio of 1 $Zn2+$ per insulin.

Where a pharmaceutically acceptable isotonicity agent is to be included in the formulations of the invention, the isotonicity agent may be selected from the group consisting of glycerol, mannitol, propylene glycol, dimethyl sulfone, methyl sulfonyl methane, trehalose, sucrose, sorbitol, saccarose and/or lactose or mixtures thereof. In a preferred embodiment of the invention the isotonicity agent is glycerol.

In a further embodiment of the invention the isotonicity agent is present in a concentration from about 0.5% to about 3%, more preferably in a concentration from about 1% to about 2%, and most preferably in a concentration from about 1.6%.

The use of an isotonicity agent in pharmaceutical compositions is well-known to the skilled person. For convenience reference is made to Remington: *The Science and Practice of Pharmacy*, 19$^{th}$ edition, 1995.

In another embodiment of the invention, a buffer may be included in the formulations of the invention.

Where a buffer is to be included in the formulations of the invention, the buffer is selected from the group consisting of sodium acetate, sodium carbonate, citrate, glycylglycine, histidine, glycine, lysine, arginin, sodium dihydrogen phosphate, disodium hydrogen phosphate, sodium phosphate, and tris(hydroxymethyl)-aminomethan, or mixtures thereof. Each one of these specific buffers constitutes an alternative embodiment of the invention. In a preferred embodiment of the invention the buffer is glycylglycine, sodium dihydrogen phosphate, disodium hydrogen phosphate, sodium phosphate or mixtures thereof. Of course, it is to be understood that where protamine acetate is the protamine salt included in the formulations of the invention, then the protamine acetate can act as a buffer. For example, if 1.0 mM protamine acetate is added to the formulations of the invention, the concentration of acetate is about 20 mM.

In a further embodiment of the invention the formulation may further comprise a stabiliser selected from the group of high molecular weight polymers or low molecular compounds where such stabilizers include, but are not limited to, polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. Each one of these specific stabilizers constitutes an alternative embodiment of the invention. In a preferred embodiment of the invention the stabiliser is selected from the group consisting of L-histidine, imidazole and arginine.

In a further embodiment of the invention the high molecular weight polymer is present in a concentration from 0.1 mg/ml to 50 mg/ml. In a further embodiment of the invention the high molecular weight polymer is present in a concentration from 0.1 mg/ml to 5 mg/ml. In a further embodiment of the invention the high molecular weight polymer is present in a concentration from 5 mg/ml to 10 mg/ml. In a further embodiment of the invention the high molecular weight polymer is present in a concentration from 0 mg/ml to 20 mg/ml. In a further embodiment of the invention the high molecular weight polymer is present in a concentration from 20 mg/ml to 30 mg/ml. In a further embodiment of the invention the high molecular weight polymer is present in a concentration from 30 mg/ml to 50 mg/ml.

In a further embodiment of the invention the low molecular weight compound is present in a concentration from 0.1 mg/ml to 50 mg/ml. In a further embodiment of the invention the low molecular weight compound is present in a concentration from 0.1 mg/ml to 5 mg/ml.

In a further embodiment of the invention the low molecular weight compound is present in a concentration from 5 mg/ml to 10 mg/ml. In a further embodiment of the invention the low molecular weight compound is present in a concentration from 10 mg/ml to 20 mg/ml. In a further embodiment of the invention the low molecular weight compound is present in a concentration from 20 mg/ml to 30 mg/ml. In a further embodiment of the invention the low molecular weight compound is present in a concentration from 30 mg/ml to 50 mg/ml.

The use of a stabilizer in pharmaceutical compositions is well-known to the skilled person. For convenience reference is made to Remington: *The Science and Practice of Pharmacy*, 19$^{th}$ edition, 1995.

In a further embodiment of the invention the formulation of the invention may further comprise a surfactant where a surfactant may be selected from a detergent, ethoxylated castor oil, polyglycolyzed glycerides, acetylated monoglycerides, sorbitan fatty acid esters, polysorbate, such as polysorbate-20, block copolymers as polyethyleneoxide/polypropyleneoxide block copolymers such as poloxamers, poloxamer 188 and poloxamer 407, Brij®35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Dodecanoyl-N-methylglucamide, alkyl-polyglucosides, ethoxylated castor oil, Heptaethylene glycol monodecyl ether, Heptaethylene glycol monododecyl ether, Heptaethylene glycol monotetradecyl ether, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O-(N-heptylcarbamoyl)-beta-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-β-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tetradecyl-β-D-maltoside, Tetraethylene glycol monodecyl ether, Tetraethylene glycol monododecyl ether, Tetraethylene glycol monotetra-decyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165 solution, Triton® X-305 solution, Triton® X-405, Triton® X-45, Triton® X-705-70, TWEEN® 20, TWEEN® 40, TWEEN® 60, TWEEN® 6, TWEEN® 65, TWEEN® 80, TWEEN® 81, TWEEN® 85, Tyloxapol, glycerol, cholic acid or derivatives thereof, lecithins, alcohols and phospholipids, glycerol-phospholipids (lecithins, kephalins, phosphatidyl serine), glycerolglycolipids (galacto-pyranosoide), sphingophospholipids (sphingomyelin), and sphingoglycollipids (ceramides, gangliosides), DSS (docusate sodium, docusate calcium, docusate potassium, SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycolcholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphateidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-gluco-pyranoside) or polymeric surfactants (TWEEN® 40, TWEEN® 80, Brij-35), fusidic acid derivatives- (e.g. sodium tauro-dihydrofusidate etc.), long-chain fatty acids and salts thereof C6-C12 (e.g. oleic acid and caprylic acid), acylcarnitines and derivatives, N$^\alpha$-acylated derivatives of lysine, arginine or histidine, or side-chain acylated derivatives of lysine or arginine, N$^\alpha$-acylated derivatives of dipeptides comprising any combination of lysine, arginine or histidine and a neutral or acidic amino acid, N$^\alpha$-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention. In a preferred embodiment of the invention the surfactant is poloxamer 188 or TWEEN® 20. In another preferred embodiment of the invention the surfactant is poloxamer 188. In another preferred embodiment of the invention the surfactant is TWEEN® 20.

In a further embodiment of the invention the surfactant is present in an amount less that 200 ppm, more preferably in an amount less that 100 ppm, and most preferably in an amount less that 50 ppm.

The use of a surfactant in pharmaceutical compositions is well-known to the skilled person. For convenience reference is made to Remington: *The Science and Practice of Pharmacy*, 19$^{th}$ edition, 1995.

The formulations of the invention may be prepared by conventional techniques, e.g. as described in Remington's Pharmaceutical Sciences, 1985 or in Remington: *The Science*

*and Practice of Pharmacy*, 19$^{th}$ edition, 1995, where such conventional techniques of the pharmaceutical industry involve dissolving and mixing the ingredients as appropriate to give the desired end product.

The present invention also relates to methods of making the formulations of the invention.

In one embodiment, the method for preparing formulations of the invention comprises:
a) preparing a solution by dissolving a divalent metal ion in water or buffer;
b) preparing a solution by dissolving the preservative in water or buffer;
c) preparing a solution by dissolving the isotonicity agent in water and buffer or;
d) preparing a solution by dissolving the surfactant in water or buffer;
e) preparing a solution by dissolving the insulin, insulin analog, insulin derivative or a mixture of the foregoing in water or buffer;
f) preparing a solution by dissolving a protamine salt in buffer or water;
g) mixing solution e) and one or more of solutions a), b), c), and d);
h) mixing solution g) with solution f); and
i) adjusting the pH of the mixture in h); to the desired pH of less than 7.0.

Figure 10:
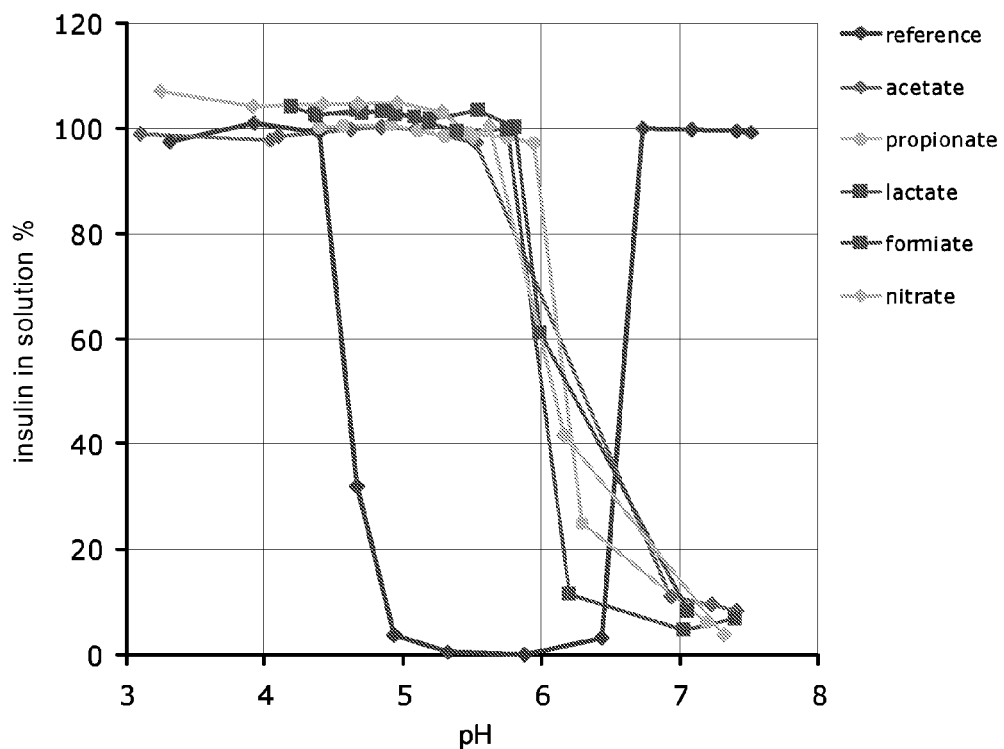
FIG. 10 shows the solubility of preparations of human insulin at various pHs where the preparations contain 100 U of insulin, 0.3 mM $Zn^{2+}$, 30 mM phenol, 1.6% glycerol and 2.0 mM of the specific protamine salt shown in the Figure for each curve. The "reference" is an insulin preparation that has the aforementioned composition except it contains no protamine salt.

In another embodiment, a solution containing insulin, an insulin analog or an insulin derivative or a mixture thereof, and optionally a preservative, an isotonicity agent and/or a divalent metal ion in water or a buffer at a pH of about 6.5 to about 7.5, preferably at about neutral pH, can be mixed with a solution of a protamine salt, and then the pH of the mixed solution can be adjusted to the desired final pH of less than 7.0.

Where the formulations of the invention contain mixtures of protamine salts such as the caproate/acetate mixture shown in FIG. 10, the solution of protamine salt to be used in the above mixtures can be prepared by dissolving each salt separately and then mixing the solutions together or by dissolving the salts together in one volume of water or buffer.

Of course, it is to be understood the components of the final formulation may be mixed together in orders other than those set forth above so long as the final formulation reaches the same equilibrium state at the end of mixing.

The present invention further relates to methods of treatment using the pharmaceutical formulations of the invention where the compositions are administered in an amount effective to combat the disease, condition, or disorder for which administration of the insulin peptide contained in the formulation is indicated.

In one embodiment, the formulations of the invention may be used in the treatment of type 1 and type 2 diabetes.

The dose, route of administration, and number of administrations per day of a formulation of the invention will be determined by a physician taking into account such factors as the therapeutic objectives, the nature and cause of the patient's disease, other drugs or medications the patient might be taking, the patient's gender and weight, level of exercise and eating habits as well as other factors that might be known to the physician.

In a broad range, the daily dose of insulin to be administered to a patient in the formulations of the invention is from about 0.1 units of insulin/kg of body weight to about 1 unit of insulin/kg of body weight.

In another embodiment, the daily dose of insulin to be administered to a patient in the formulations of the invention is from about 0.2 units of insulin/kg of body weight to about 0.6 units of insulin/kg of body weight. Of course, the physician of ordinary skill in treating diabetes would understand that the concentration ranges of insulin used to treat a diabetic patient may vary depending on whether, for example, the patient to be treated is a child with type 1 diabetes or an adult with strongly insulin resistant type 2 diabetes. The physician of ordinary skill in treating diabetes will also be able to select the therapeutically most advantageous method for administering the formulations of the invention.

In one embodiment, the formulations may be administered parenterally where typical routes of parenteral administration are subcutaneous and intramuscular. In another embodiment, the formulations may be administered parenterally where the route is subcutaneous.

In another embodiment, the formulations may be administered by nasal, buccal, pulmonary or ocular routes. In another embodiment, the formulations may be administered by nasal route. In another embodiment, the formulations may be administered by pulmonary route.

In one embodiment the formulations of the invention are used in connection with insulin pumps. The insulin pumps may be prefilled and disposable, or the insulin formulations may be supplied from a reservoir which is removable. Insulin pumps may be skin-mounted or carried, and the path of the insulin preparation from the storage compartment of the pump to the patient may be more or less tortuous. Non-limiting examples of insulin pumps are disclosed in U.S. Pat. No. 5,957,895, U.S. Pat. No. 5,858,001, U.S. Pat. No. 4,468,221, U.S. Pat. No. 4,468,221, U.S. Pat. No. 5,957,895, U.S. Pat. No. 5,858,001, U.S. Pat. No. 6,074,369, U.S. Pat. No. 5,858,001, U.S. Pat. No. 5,527,288, and U.S. Pat. No. 6,074,369.

In another embodiment the formulations of the invention are used in connection with pen-like injection devices, which may be prefilled and disposable, or the insulin formulations may be supplied from a reservoir which is removable. Non-limiting examples of pen-like injection devices are Flex-Pen®, InnoLet®, InDuo™, Innovo®.

In a further embodiment, formulations of the invention are used in connection with devices for pulmonary administration of aqueous insulin formulations, a non-limiting example of which is the AerX® device.

The invention furthermore relates to treatment of a patient in which the pharmaceutical formulations of the invention are combined with another form of treatment.

In one aspect of the invention, treatment of a patient with the pharmaceutical formulations of the invention is combined with diet and/or exercise.

In another aspect of the invention the pharmaceutical formulations of the invention are administered in combination with one or more further active substances in any suitable ratios where "in combination with" as used in connection with the pharmaceutical formulations of the invention and one or more further active substances means that the one or more further active substances may be included within the formulation of the invention or they may be contained in separate formulation(s) from the formulation of the invention. Such further active substances may e.g. be selected from antiobesity agents, antidiabetics, antihypertensive agents, agents for the treatment of complications resulting from or associated with diabetes and agents for the treatment of complications and disorders resulting from or associated with obesity.

Thus, in a further aspect of the invention the pharmaceutical formulations of the invention may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1, glp-1 analogues or derivatives hereof and ciliary neurotrophic factor.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

The orally active hypoglycemic agents comprise imidazolines, sulphonylureas, biguanides, meglitinides, oxadiazolidinediones, thiazolidinediones, insulin sensitizers, insulin secretagogues such as glimepride, α-glucosidase inhibitors, agents acting on the ATP-dependent potassium channel of the β-cells eg potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00/42026 (Novo Nordisk NS and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In a further embodiment of the invention the pharmaceutical formulations of the invention are administered in combination with a sulphonylurea e.g. tolbutamide, chlorpropamide, tolazamide, glibenclamide, glipizide, glimepiride, glicazide or glyburide.

In another embodiment of the invention the pharmaceutical formulations of the invention are administered in combination with a biguanide, e.g. metformin.

In yet another embodiment of the invention the pharmaceutical formulations of the invention are administered in combination with a meglitinide eg repaglinide or nateglinide.

In still another embodiment of the invention the pharmaceutical formulations of the invention are administered in combination with a thiazolidinedione insulin sensitizer, e.g. troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the pharmaceutical formulations of the invention may be administered in combination with an insulin sensitizer, e.g. such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention the pharmaceutical formulations of the invention are administered in combination with an α-glucosidase inhibitor, e.g. voglibose, emiglitate, miglitol or acarbose.

In another embodiment of the invention the pharmaceutical formulations of the invention are administered in combination with an agent acting on the ATP-dependent potassium channel of the β-cells, e.g. tolbutamide, glibenclamide, glipizide, glicazide, BTS-67582 or repaglinide.

In yet another embodiment of the invention the pharmaceutical formulations of the invention may be administered in combination with nateglinide.

In still another embodiment of the invention the pharmaceutical formulations of the invention are administered in combination with an antilipidemic agent, e.g. cholestyramine, colestipol, clofibrate, gemfibrozil, lovastatin, pravastatin, simvastatin, probucol or dextrothyroxine.

In another aspect of the invention, the pharmaceutical formulations of the invention are administered in combination with more than one of the above-mentioned compounds, e.g. in combination with metformin and a sulphonylurea such as glyburide; a sulphonylurea and acarbose; nateglinide and metformin; acarbose and metformin; a sulphonylurea, metformin and troglitazone; metformin and a sulphonylurea; etc.

Furthermore, the pharmaceutical formulations of the invention may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicerdipine, isradipine, nimodipine, diltiazem and verapamil, and α-blockers such as doxazosin, urapidil, prazosin and terazosin. The pharmaceutical preparation of the invention may also be combined with $N^eP$ inhibitors such as candoxatril.

Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with diet and/or exercise, one or more of the above-mentioned compounds and optionally one or more other active substances are considered to be within the scope of the present invention.

All scientific publications and patents cited herein are specifically incorporated by reference. The following examples illustrate various aspects of the invention but are in no way intended to limit the scope thereof.

EXAMPLES

Example 1

Chemical Stability of Protamine Acetate-Containing Insulin Formulations

Figure 1A:
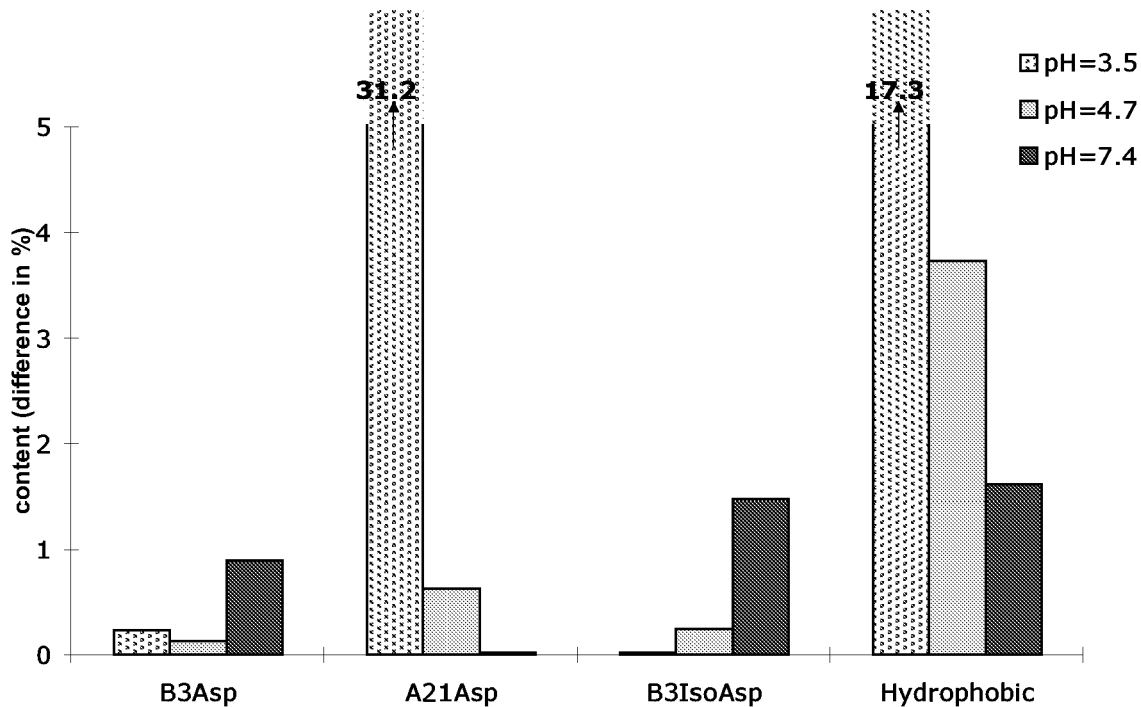
FIGS. 1A and 1B show the increase in content (in percent of total insulin content) of deamidation products (B3Asp, B3isoAsp, A21 Asp) and hydrophobic products (mainly covalent aggregates) after 14 days at 3° C. at various pHs as compared to start for insulin preparations without protamine acetate (FIG. 1A; 0.6 mM human insulin, 0.3 mM Zn2+, 30 mM phenol, 1.6% glycerol, pH=3.5, 4.7 and 7.4) and with protamine acetate (FIG. 1B; 0.6 mM human insulin, 0.3 mM Zn2+, 30 mM phenol, 1.6% glycerol, 1.6 mM protamine-acetate, pH=5.0 and pH=5.5)
Figure 1B:
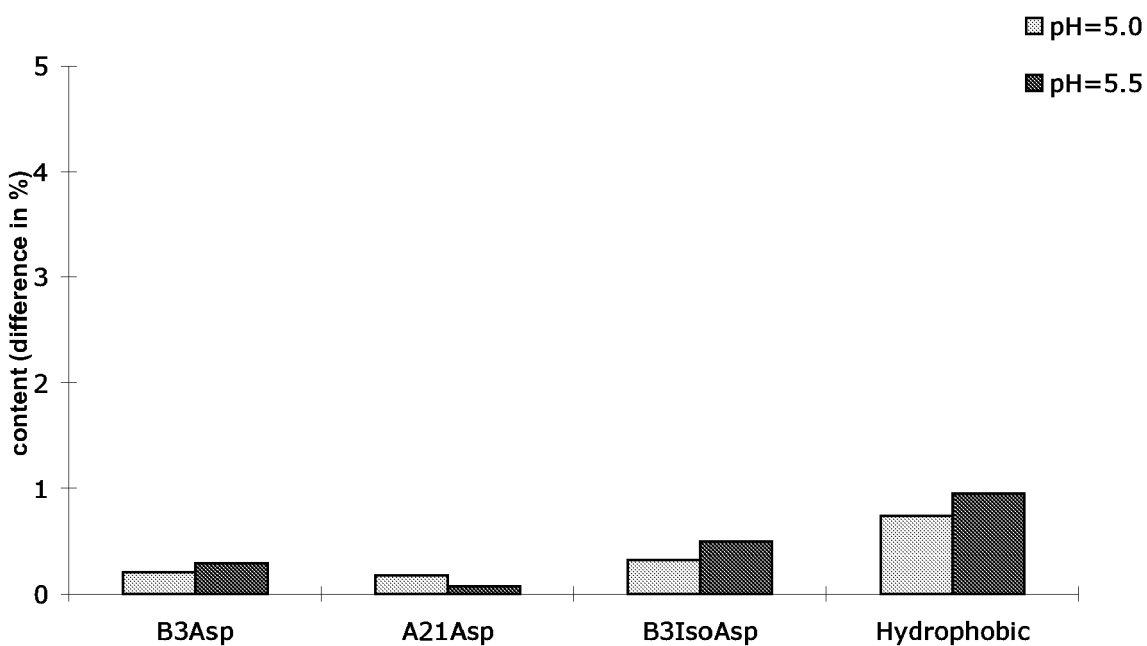

The chemical stability at various pHs of preparations of human insulin without (FIG. 1A 0.6 mM human insulin, 0.3 mM Zn2+, 30 mM phenol, 1.6% glycerol, pH=3.5, 4.7 and 7.4) or with (FIG. 1B 0.6 mM human insulin, 0.3 mM Zn2+, 30 mM phenol, 1.6% glycerol, 1.6 mM protamine-acetate, pH=5.0 and pH=5.5) protamine acetate was assessed by measurement of the increase in content (in percent of total insulin content) of deamidation products (B3Asp, B3isoAsp, A21 Asp) and hydrophobic products (mainly covalent aggregates) after 14 days at 37° C. compared to start (14 days at 37° C. being comparable to 2 years at 4° C.). The preparations were analysed by reverse phase HPLC on a Kromasil C4 column, 150×4.6 mm ID, 5 micron particle size, eluted at 1 ml/minute at 35° C. The monomeric insulin compounds are eluted isocratically with a phosphate buffer, pH3.4 containing sodium sulphate and approximately 30% (v/v) acetonitrile followed by a gradient step with increased acetonitrile concentration for elution of the more hydrophobic compounds.

Example 2

Equilibrium Solubility of Protamine Acetate-Containing Insulin Formulations

For pH-solubility profiles, 0.6 mM human insulin stock solutions containing 0.0-0.6 mM $Zn^{2+}$, 30 mM phenol, 1.6% glycerol and 0.7 mM protamine-sulphate or 0.0-2.0 mM protamine-acetate were prepared and the pH was adjusted to the desired value corresponding to the alkaline endpoint of the pH-solubility profile. From these stock solutions samples were withdrawn, the pH adjusted to the desired value in the pH 3-8 range, and 0.3 ml samples were incubated at 23° C. for at least 4 days. After centrifugation (20,000 g for 20 minutes at 23 C) of each sample, pH was measured and the solubility was determined by quantification of insulin contents in the supernatant by SEC HPLC analysis similar to the one described in Example 1.

Figure 2A:
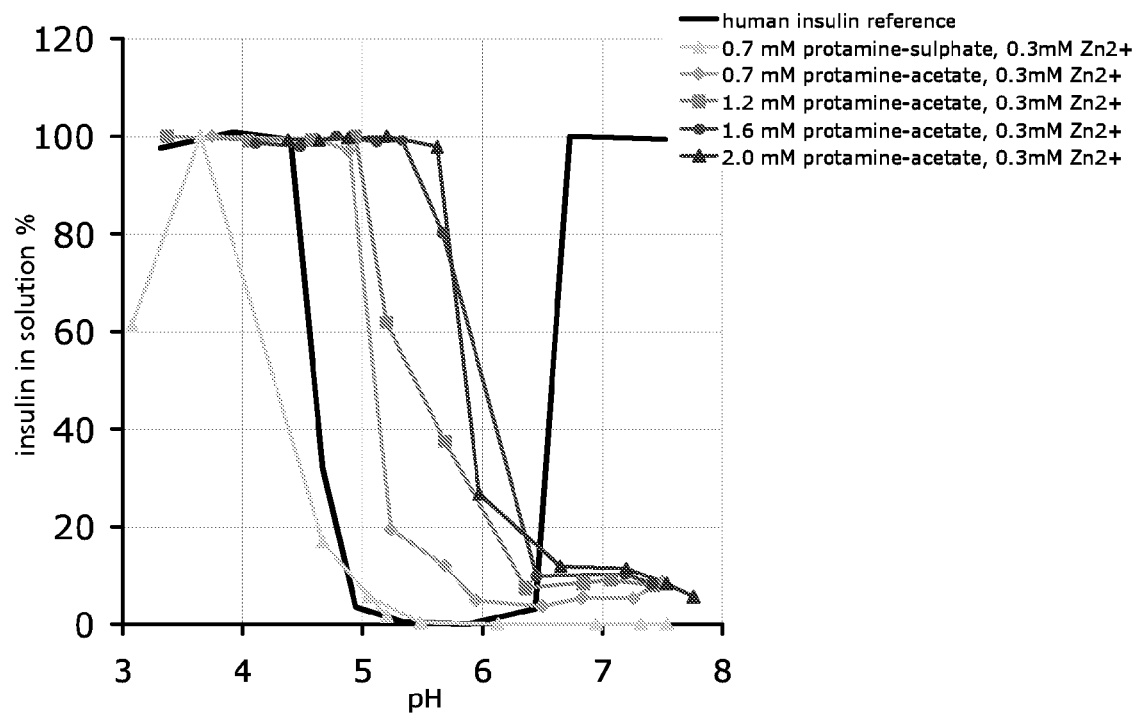
FIGS. 2A-C show the effects of different concentrations of protamine salt and zinc on the pH-dependence of insulin solubility in human insulin preparations, where in all three Figures (ie FIGS. 2A-2C), the human insulin reference is 0.6 mM human insulin, 0.3 mM Zn2+, 30 mM phenol, 1.6% glycerol.
Figure 2B:
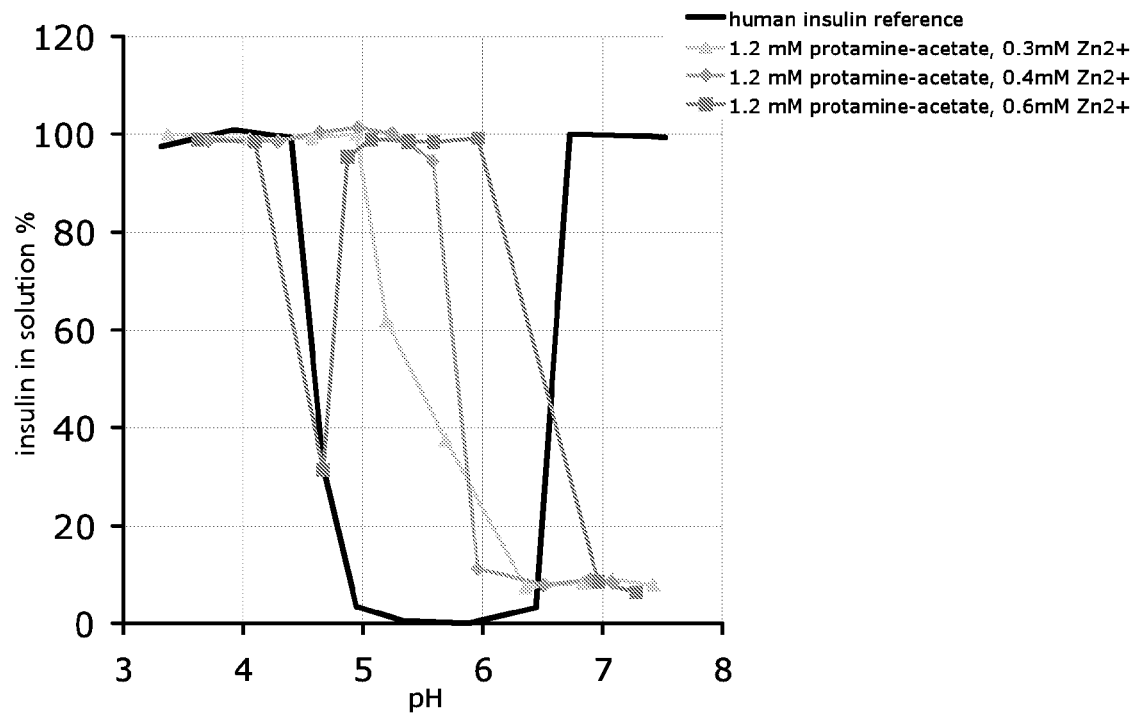
Figure 2C:
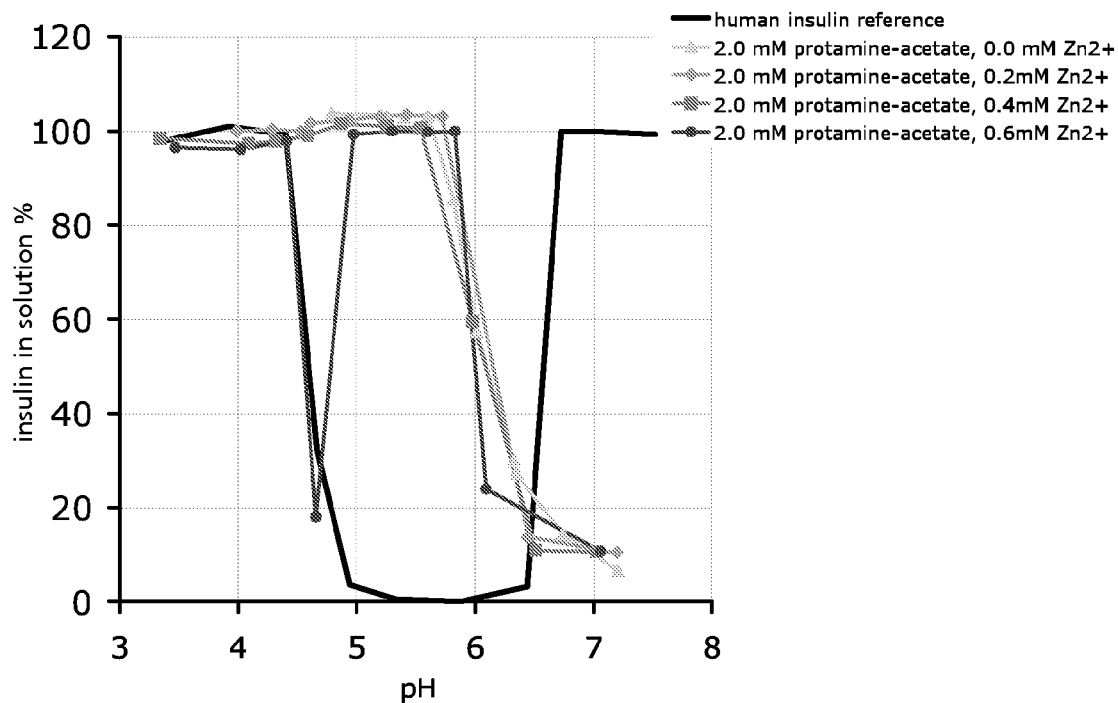

The effect of different concentrations of protamine salt and zinc on the pH-dependence of insulin solubility in various insulin preparations is shown in FIGS. 2A-2C.

In FIG. 2A the pH-dependence of various human insulin formulations containing 0.6 mM human insulin, 0.3 mM Zn2+, 30 mM phenol, 1.6% glycerol, and 0.7 mM protamine-sulphate or 0.7-2.0 mM protamine-acetate is shown. In FIG. 2B, the pH-dependence of various human insulin formulations containing 0.6 mM human insulin, 30 mM phenol, 1.6% glycerol, 1.2 mM protamine-acetate, and 0.3-0.6 mM Zn2+ is shown. In FIG. 2C, the pH-dependence of various human insulin formulations containing 0.6 mM human insulin, 30 mM phenol, 1.6% glycerol, 2.0 mM protamine-acetate, and 0.0-0.6 mM Zn2+ is shown. In FIGS. 2A-2C, the human insulin reference is 0.6 mM human insulin, 0.3 mM Zn2+, 30 mM phenol, 1.6% glycerol.

Example 3

Testing of Insulin Containing Formulations in Pigs

Pharmacodynamic (PD) studies using the following insulin formulations were performed on domestic female pigs, LYD cross-breed, weighing between 55 and 110 kg:
1) 0.6 mM human insulin, 0.3 mM Zn2+, 30 mM phenol, 1.6% glycerol, 1.0 mM protamine-acetate, pH=5.0;
2) 0.6 mM human insulin, 0.3 mM Zn2+, 30 mM phenol, 1.6% glycerol, 2.0 mM protamine-acetate, pH=5.0;
3) 0.6 mM human insulin, 0.6 mM Zn2+, 30 mM phenol, 1.6% glycerol, 1.0 mM protamine-acetate, pH=5.0; and
4) 0.6 mM human insulin, 0.6 mM Zn2+, 30 mM phenol, 1.6% glycerol, 2.0 mM protamine-acetate, pH=5.0.

The pigs were catheterised into the jugular vein through an ear vein at least 2 days before start of the study. The last meal before the start of the study was served to the animals approximately 18 hours prior to the injection of the insulin formulation, and the animals had free access to water at all time during the fasting period and the test period.

At time 0 hours the insulin formulation was given subcutaneously at 0.2 units of insulin/kg on the lateral side of the neck. At regular time intervals blood samples were drawn from the catheter and sampled into 1.5 ml glass tubes pre-coated with heparin. The blood samples were kept in ice water until separation of plasma by centrifugation for 10 minutes at 3000 rpm at 4° C., which was done within the first 30 minutes. Plasma samples were stored at 4° C. for short time (2-3 hours) or at −18° C. for long term storage and were analysed for glucose on COBAS MIRA. Estimation of start level of glucose in blood was done on 4 samples taken 1 hour, half an hour, 20 minutes and immediately before injection.

Figure 3:
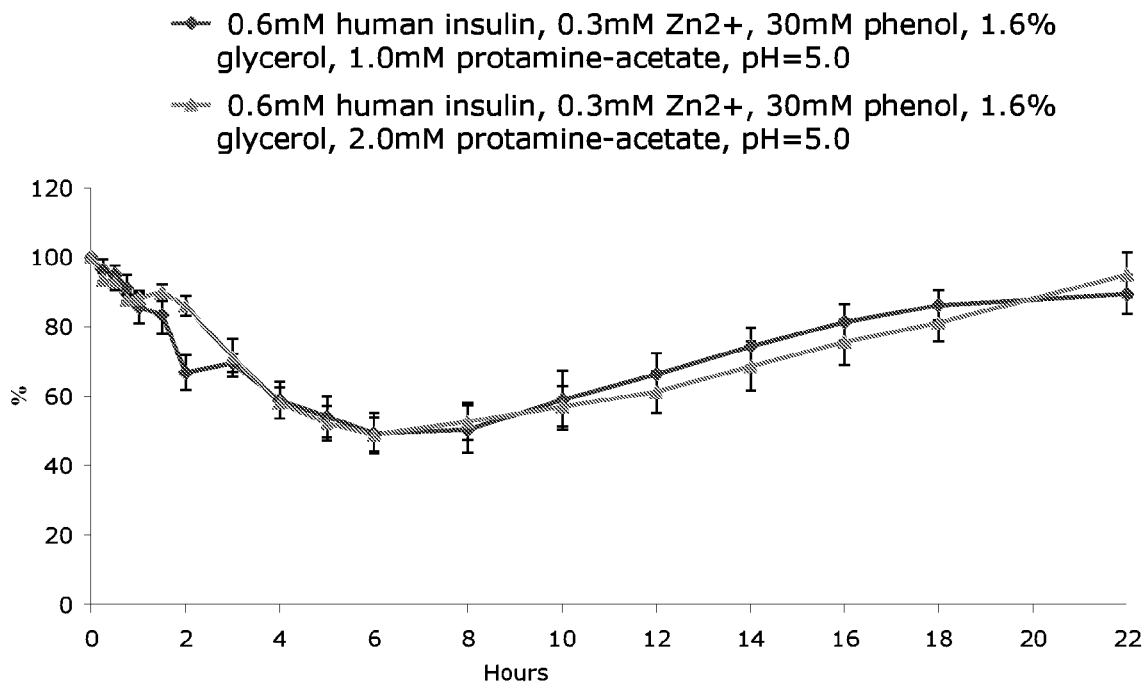
FIG. 3 shows the change in plasma glucose level (% of baseline) (average+/−SEM of N pigs) after subcutaneous injection at 0 hours of the following preparations of human insulin: 0.6 mM human insulin, 0.3 mM Zn2+, 30 mM phenol, 1.6% glycerol, 1.0 mM protamine-acetate, pH=5.0 (N=6), and 0.6 mM human insulin, 0.3 mM Zn2+, 30 mM phenol, 1.6% glycerol, 2.0 mM protamine-acetate, pH=5.0 (N=6).

FIG. 3 shows the change in plasma glucose level (% of baseline) (average+/−SEM of N pigs) after subcutaneous injection at 0 hours of the following human insulin preparations: 0.6 mM human insulin, 0.3 mM Zn2+, 30 mM phenol, 1.6% glycerol, 1.0 mM protamine-acetate, pH=5.0 (N=6), and 0.6 mM human insulin, 0.3 mM Zn2+, 30 mM phenol, 1.6% glycerol, 2.0 mM protamine-acetate, pH=5.0 (N=6).

Figure 4:
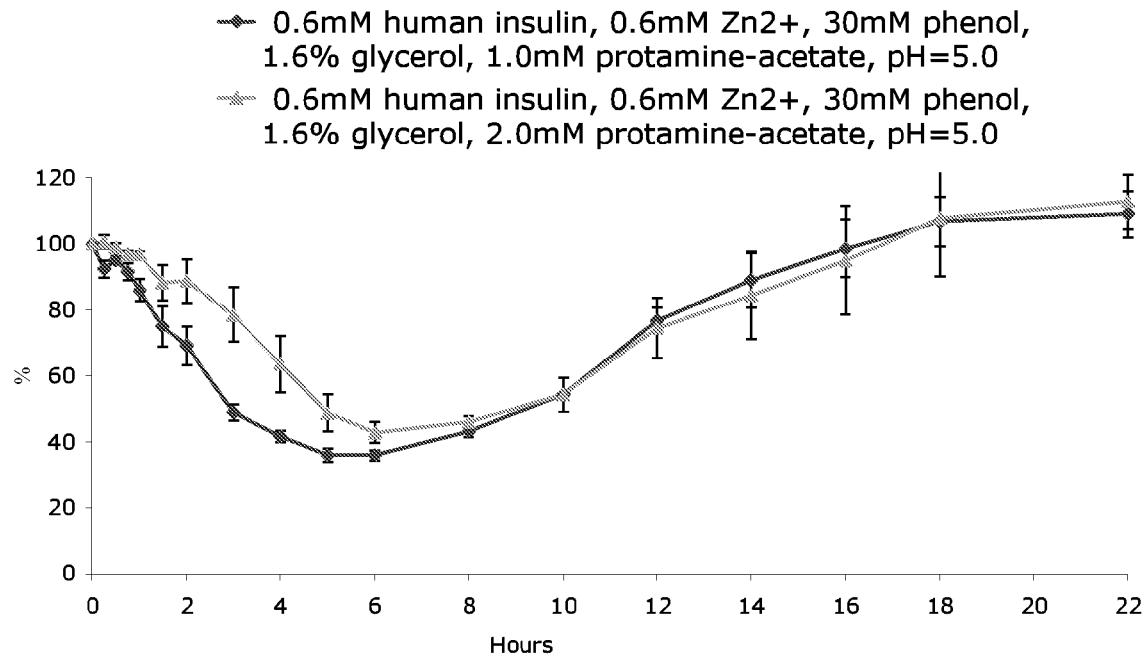
FIG. 4 shows the change in plasma glucose level (% of baseline) (average+/−SEM of N pigs) after subcutaneous injection at 0 hours of the following preparations of human insulin: 0.6 mM human insulin, 0.6 mM Zn2+, 30 mM phenol, 1.6% glycerol, 1.0 mM protamine-acetate, pH=5.0 (N=6), and 0.6 mM human insulin, 0.6 mM Zn2+, 30 mM phenol, 1.6% glycerol, 2.0 mM protamine-acetate, pH=5.0 (N=5).
Figure 5:
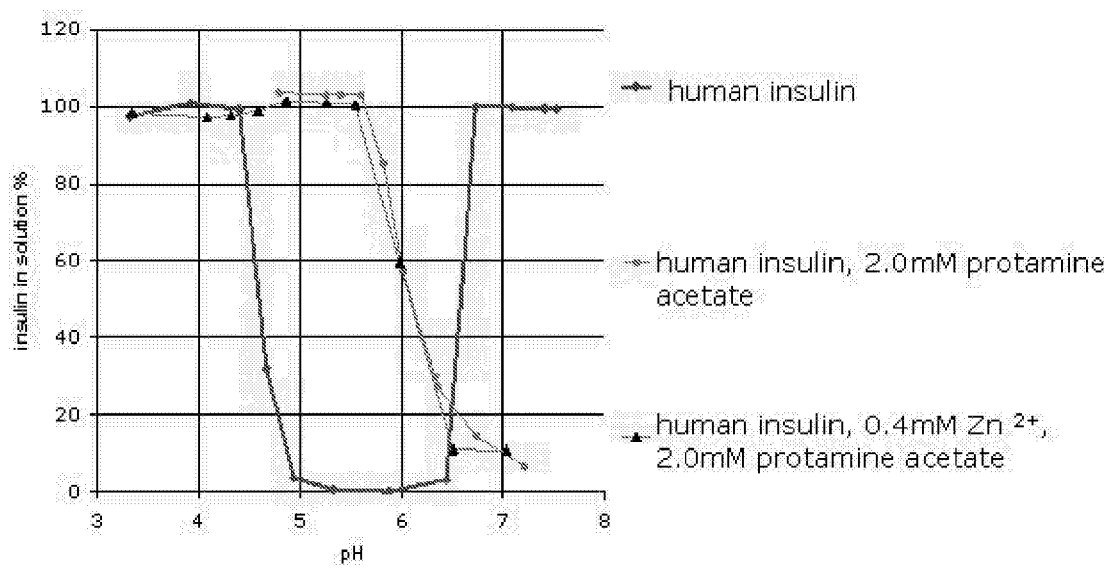
FIG. 5 shows the effect of protamine acetate on the solubility of human insulin preparations. Preparations are 0.6 mM human insulin, 30 mM phenol, and 1.6% glycerol ("human insulin") with addition of 2.0 mM protamine acetate ("human insulin, 2.0 mM protamine acetate") or 2.0 mM protamine acetate and 0.4 mM $Zn^{2+}$ ("human insulin, 0.4 mM $Zn^{2+}$, 2.0 mM protamine acetate").
Figure 6:
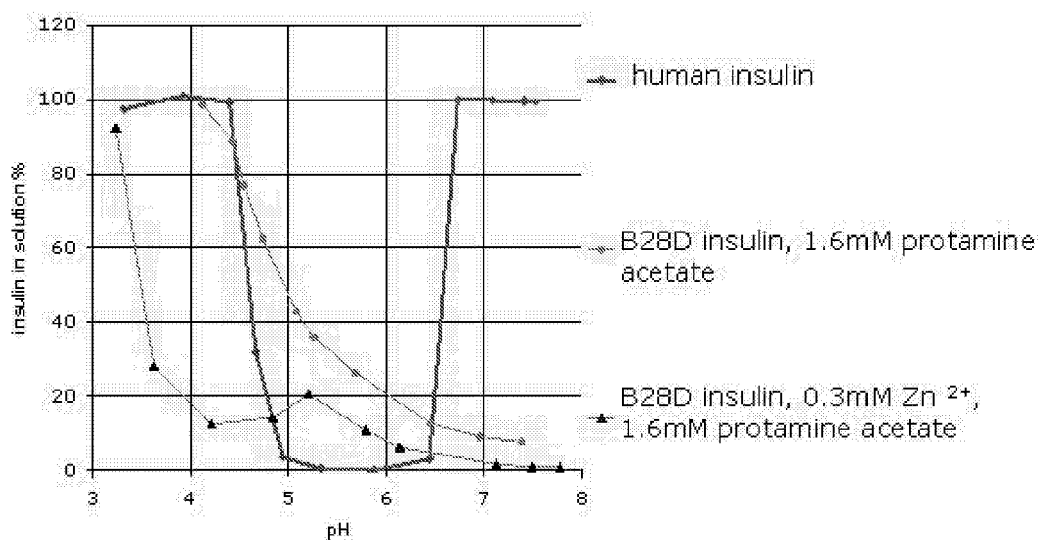
FIG. 6 shows the effect of protamine acetate on the solubility of human insulin and B28D human insulin preparations. Preparations are 0.6 mM human insulin, 30 mM phenol and 1.6% glycerol with addition of 0.3 mM $Zn^{2+}$ ("human insulin") or 0.6 mM B28D human insulin, 30 mM phenol and 1.6% glycerol with addition of 1.6 mM protamine acetate ("B28D insulin, 1.6 mM protamine acetate") or 1.6 mM protamine acetate and 0.3 mM $Zn^{2+}$ ("B28D insulin, 0.3 mM $Zn^{2+}$, 1.6 mM protamine acetate").
Figure 7:
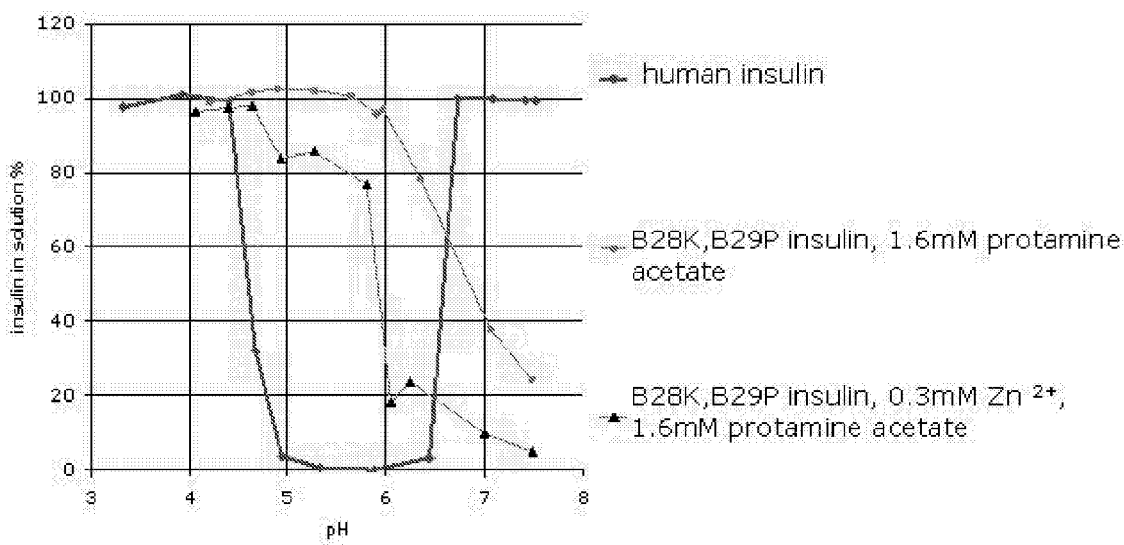
FIG. 7 shows the effect of protamine acetate on the solubility of human insulin and B28K, B29P human insulin preparations. Preparations are 0.6 mM human insulin, 30 mM phenol and 1.6% glycerol with addition of 0.3 mM $Zn^{2+}$ ("human insulin") or 0.6 mM B28K, B29P human insulin, 30 mM phenol and 1.6% glycerol with addition of 1.6 mM protamine acetate ("B28K, B29P insulin, 1.6 mM protamine acetate") or 1.6 mM protamine acetate and 0.3 mM $Zn^{2+}$ ("B28K, B29P insulin, 0.3 mM $Zn^{2+}$, 1.6 mM protamine acetate").
Figure 8:
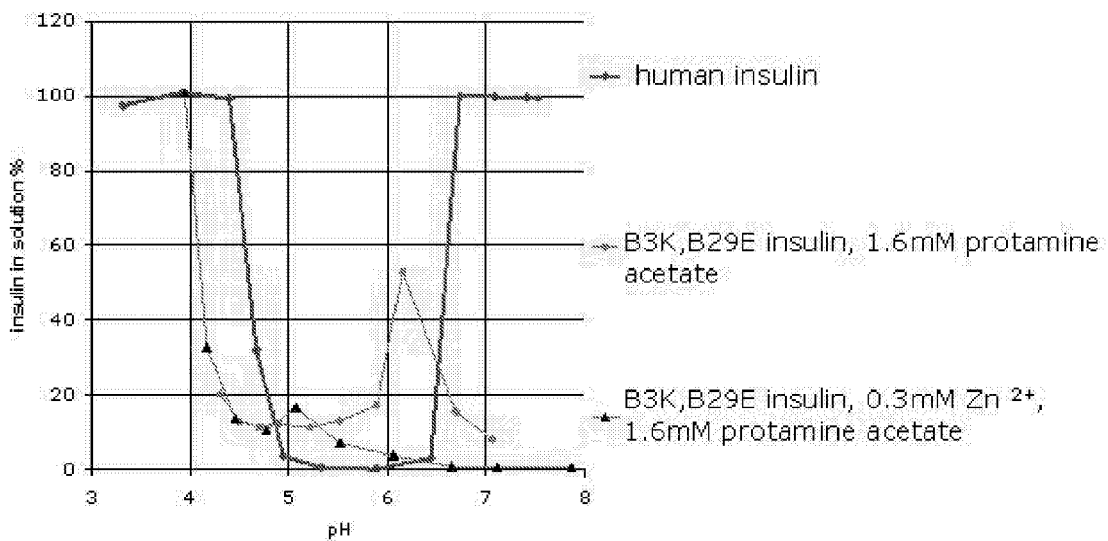
FIG. 8 shows the effect of protamine acetate on the solubility of human insulin and B3K, B29E human insulin preparations. Preparations are 0.6 mM human insulin, 30 mM phenol and 1.6% glycerol with addition of 0.3 mM $Zn^{2+}$ ("human insulin") or 0.6 mM B3K, B29E human insulin, 30 mM phenol and 1.6% glycerol with addition of 1.6 mM protamine acetate ("B3K, B29E insulin, 1.6 mM protamine acetate") or 1.6 mM protamine acetate and 0.3 mM $Zn^{2+}$ ("B3K, B29E insulin, 0.3 mM $Zn^{2+}$, 1.6 mM protamine acetate").
Figure 9:
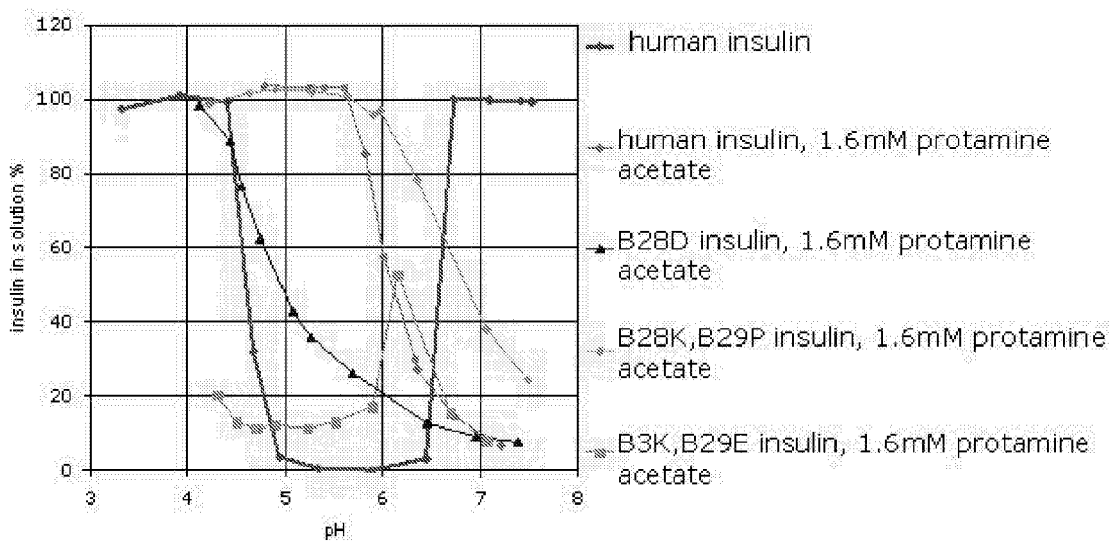
FIG. 9 is a compilation of the data from FIGS. 5-8 that shows the effect of protamine acetate on the solubility of human insulin, B28D human insulin, B28K, B29P human insulin and B3K, B29E human insulin. Preparations are 0.6 mM human insulin, 30 mM phenol and 1.6% glycerol ("human insulin") or 0.6 mM B28D human insulin, B28K, B29P human insulin or B3K, B29E human insulin, 30 mM phenol and 1.6% glycerol with addition of 1.6 mM protamine acetate.

FIG. 4 shows the change in plasma glucose level (% of baseline) (average+/−SEM of N pigs) after subcutaneous injection at 0 hours of the following human insulin preparations: 0.6 mM human insulin, 0.6 mM Zn2+, 30 mM phenol, 1.6% glycerol, 1.0 mM protamine-acetate, pH=5.0 (N=6), and 0.6 mM human insulin, 0.6 mM Zn2+, 30 mM phenol, 1.6% glycerol, 2.0 mM protamine-acetate, pH=5.0 (N=5).

Example 4

Testing the Solubility vs pH Profiles of Commercially Marketed Insulins in the Presence of Protamine Acetate FIGS. 5-9 show the solubility of commercially marketed insulins (human insulin, B28D human insulin (Aspart), B28K, B29P human insulin (LysPro) and B3K, B29E human insulin (Glulisine) in the presence of 1.6 mM protamine acetate. In each figure a reference curve of human insulin without protamine salt is present demonstrating the precipitation zone of human insulin in the pH range between ~4.5 and ~6.5. The data in FIGS. 5-9 show that protamine acetate solubilizes human insulin (FIG. 5) and LysPro insulin (FIG. 7) to the greatest degree of the insulins tested.

Example 5

Figure 11:
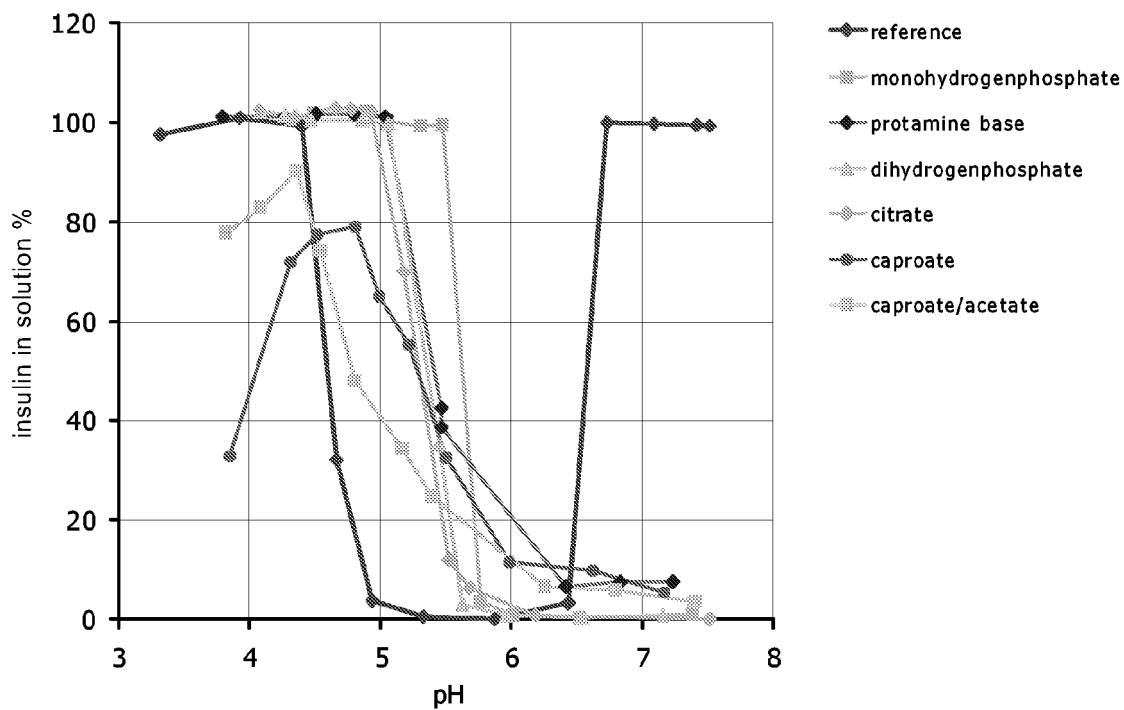
FIG. 11 shows the solubility of preparations of human insulin at various pHs where the preparations contain 100 U of insulin, 0.3 mM $Zn^{2+}$, 30 mM phenol, 1.6% glycerol and 2.0 mM of the specific protamine salt shown in the Figure for each curve (for the caproate/-acetate mixture, it is 0.5 mM caproate and 1.5 mM acetate). The "reference" is an insulin preparation that has the aforementioned composition except it contains no protamine salt.
Figure 12:
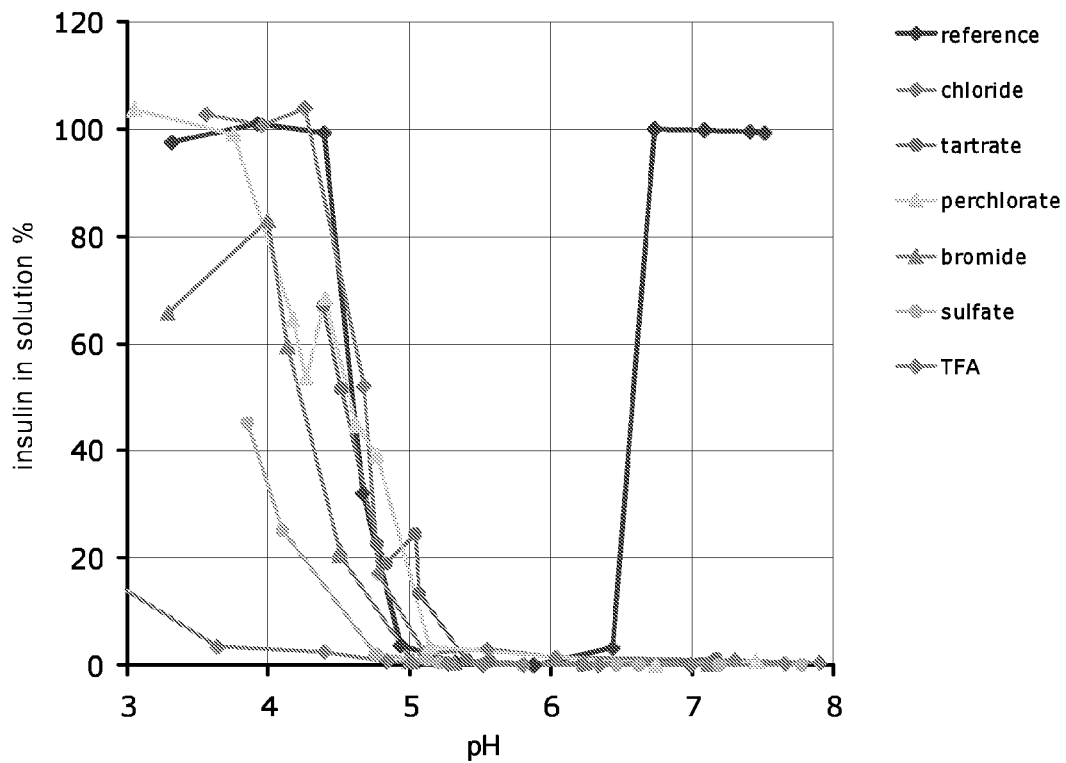
FIG. 12 shows the solubility of preparations of human insulin at various pHs where the preparations contain 100 U of insulin, 0.3 mM $Zn^{2+}$, 30 mM phenol, 1.6% glycerol and 2.0 mM of the specific protamine salt shown in the Figure for each curve. The "reference" is an insulin preparation that has the aforementioned composition except it contains no protamine salt.

Testing the Solubility vs. pH Profiles of Human Insulin in the Presence of 15 Different Protamine Salts FIGS. 10-12 show the solubility of human insulin in the presence of different protamine salts. In each figure a reference curve of human insulin without protamine salt is present demonstrating the precipitation zone of human insulin in the pH range between ~4.5 and ~6.5.

Of the salts tested, propionate, lactate, formiate, nitrate and acetate give the best solubility of human insulin in the pH range of ~4.5 to ~6.0.

Example 6

Effects of Temperature and Time of storage on the Solubility of Various Preparations of Human Insulin at Different pHs FIGS. 13-17 show that increasing storage temperature narrows the range of pH values where solubility of the insulin preparations is observed but that any precipitation of insulin observed at higher temperatures can be reversed by lowering the temperature at which the preparations are stored.

Example 7

Glucose Utilization of Preparations of Human Insulin

The glucose utilization effect following a subcutaneous injection of the insulin preparations of the present invention were characterized using a pig clamp model as described in Kurtzhals & Ribel, Diabetes 44, 1381-1385, (1995).

Figure 18:
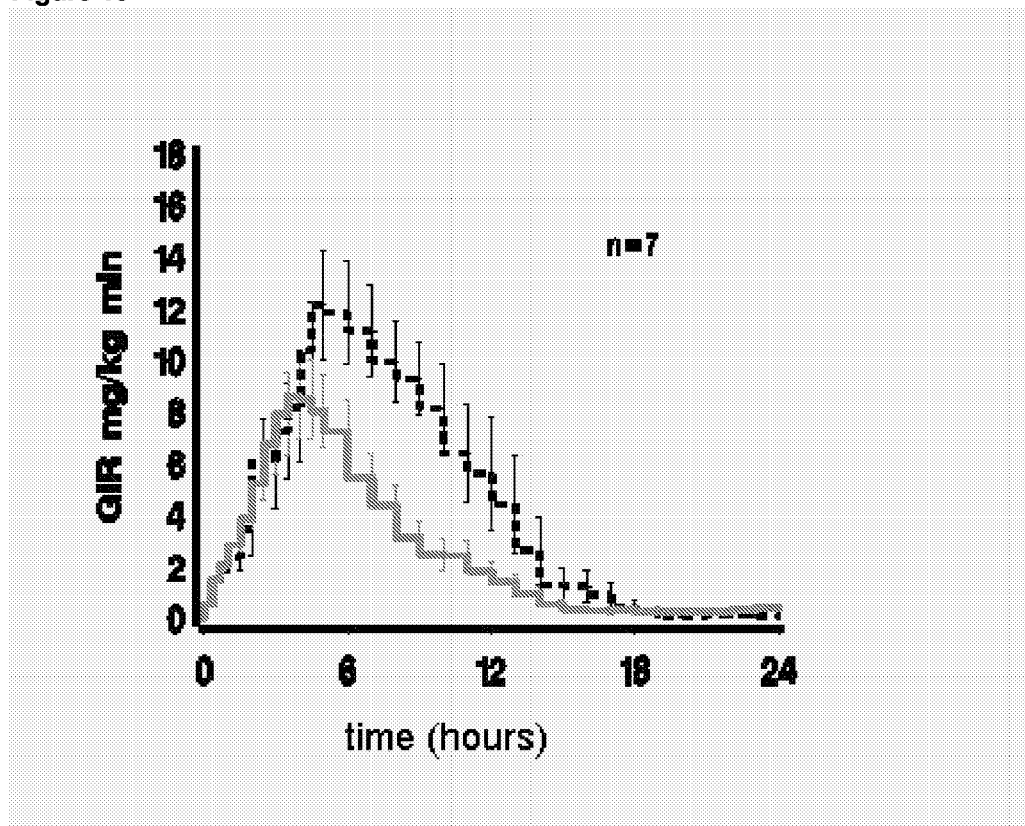
FIG. 18 shows glucose utilization by pigs after subcutaneous injection with either 216 nmol of regular NPH (Insulatard) (7 pigs, data shown in grey) or with 216 nmol of a preparation of 0.6 mM human insulin, 1.0 mM protamine acetate, 30 mM phenol, 1.6% glycerol, pH=5.0. The glucose infusion rate (GIR) is expressed as means±SE.

FIG. 18 compares glucose utilization in pigs following subcutaneous injection with either an NPH insulin preparation or a preparation of 0.6 mM human insulin, 1.0 mM protamine acetate, 30 mM phenol, 1.6% glycerol, pH=5.0 and shows that increased glucose utilization is observed upon injection of the latter preparation.

Example 8

Preparation of Protamine Acetate by Precipitation of Barium Sulphate 10 gram of protamine sulphate was dissolved by agitation in 1 liter of distilled water heated to 60° C. 4.8 gram of barium acetate was then dissolved herein and the resulting suspension was left for 16 hours at 4° C. with gentle agitation. The suspension was centrifuged at 6000 rpm for 20 minutes at 4° C. and the supernatant was filtrated through 0.22 µm filter and lyophilized. Yield: 9.3 gram of Protamine Acetate.

Example 9

Preparation of Protamine Acetate by Anion Exchange 10 gram of protamine sulphate was dissolved by agitation in 1 liter of distilled water heated to 60° C. and cooled to ambient temperature. A 1.6×20 cm column of AG 1×8 Resin anion exchanger (100-200 mesh, acetate form (BioRad Inc., cat. no. 140-1443) was packed and flushed with 120 ml of distilled water. The protamine sulphate solution was then led through the column at a flow of 60 ml per hour and the eluate collected. The column was finally eluted with 100 ml of distilled water and the collected eluates were filtrated through 0.22 µm filter and lyophilized. Yield: 9.4 gram of Protamine Acetate.

It would be understood by one of ordinary skill in the art that the methods described in Examples 8 and 9 could be used to convert protamine sulphate to any salt form of choice by use of the appropriate barium salt (Example 8) or anion exchange resin form (Example 9)

Example 10

Figure 19:
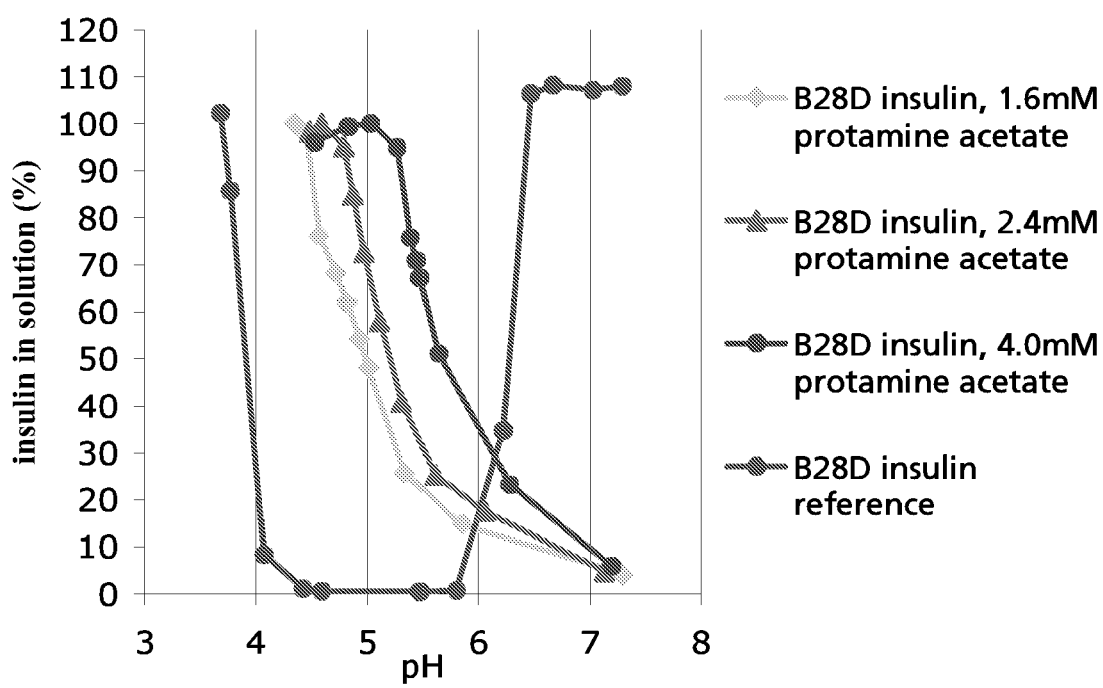
FIGS. 19 and 20 show the solubility of B28D insulin in the presence of 1.6 mM to 4.0 mM concentrations of protamine acetate. In each figure a curve of B28D insulin without protamine salt is present demonstrating the precipitation zone of B28D insulin in the pH range between pH~3.8 and ~6.5.
Figure 20:
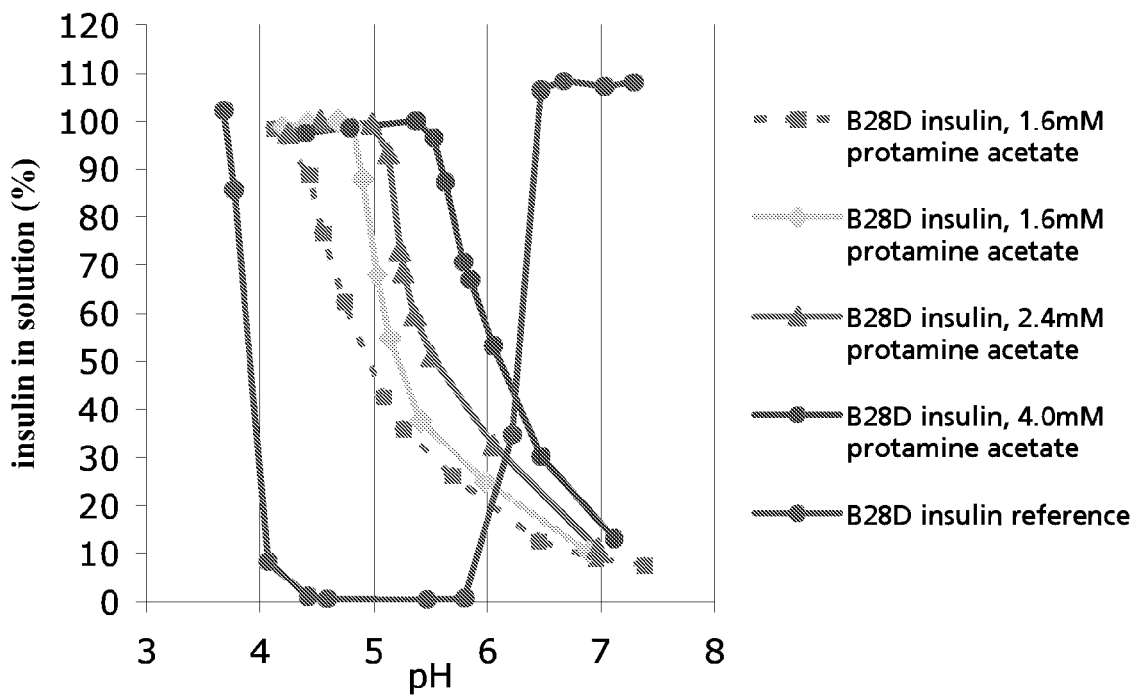

Testing the Solubility vs. pH of B28D Insulin in the Presence of Higher Concentrations of Protamine Acetate FIGS. 19 and 20 show the solubility of B28D insulin in the presence of 1.6 mM to 4.0 mM concentrations of protamine acetate. In each figure a curve of B28D insulin without protamine salt is present demonstrating the precipitation zone of B28D insulin in the pH range between pH~3.8 and ~6.5.

The data demonstrates that B28D insulin is solubilized by protamine acetate in the pH range up to ~5.3 with a concentration of protamine acetate high relative to the concentration needed to solubilize human insulin or B28K, B29P insulin in the same pH range.

Compositions of preparations in FIG. 19 are 1.3 mM B28D insulin, 25 mM m-cresol, 1.6% glycerol, 40 ppm TWEEN® 20 with protamine acetate concentrations 1.6-2.4-4.0 mM. B28D insulin reference is 0.6 mM B28D insulin, 0.3 mM $Zn^{2+}$, 30 mM phenol.

Compositions of preparations in FIG. 20 are 0.6 mM B28D insulin, 30 mM phenol, 1.6% glycerol, 40 ppm, 1.6 mM protamine acetate and 0.6 mM B28D insulin, 25 mM m-cresol, 1.6% glycerol, 40 ppm TWEEN® 20 with protamine acetate concentrations 1.6-2.4-4.0 mM. B28D insulin reference is 0.6 mM B28D insulin, 0.3 mM $Zn^{2+}$, 30 mM phenol.

Example 11

Figure 21:
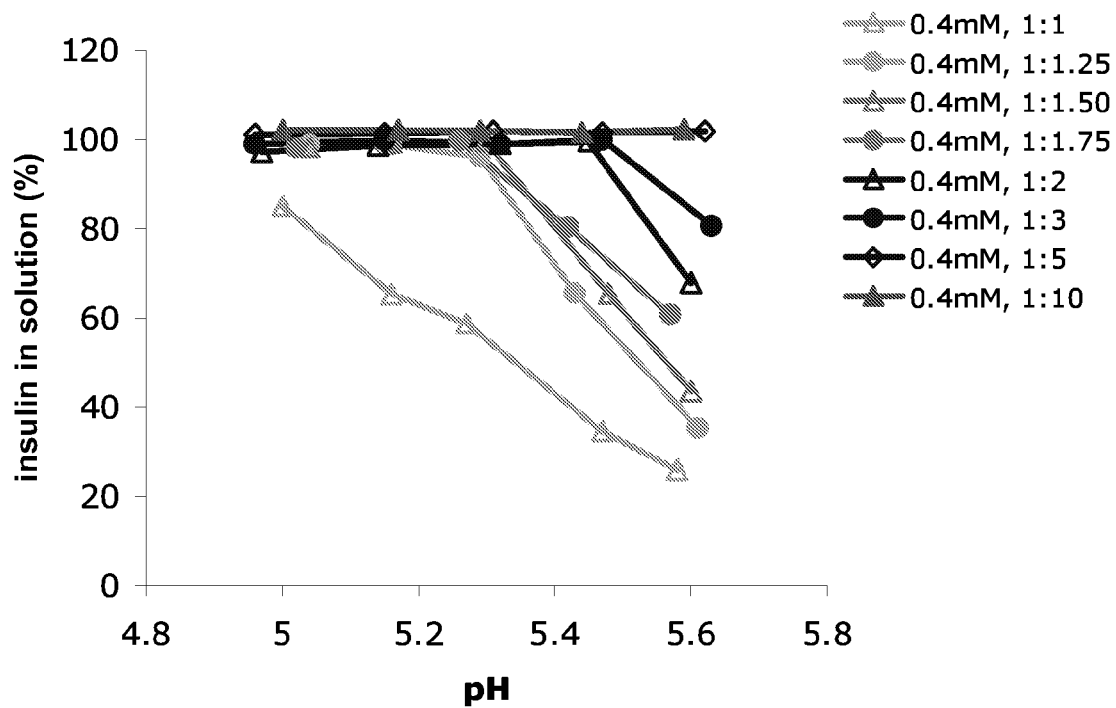
FIGS. 21-23 show the solubility of human insulin at three different concentrations in the presence of varying concentrations of protamine acetate. The solubility is measured after incubation of samples for 14 days at 37° C.
Figure 22:
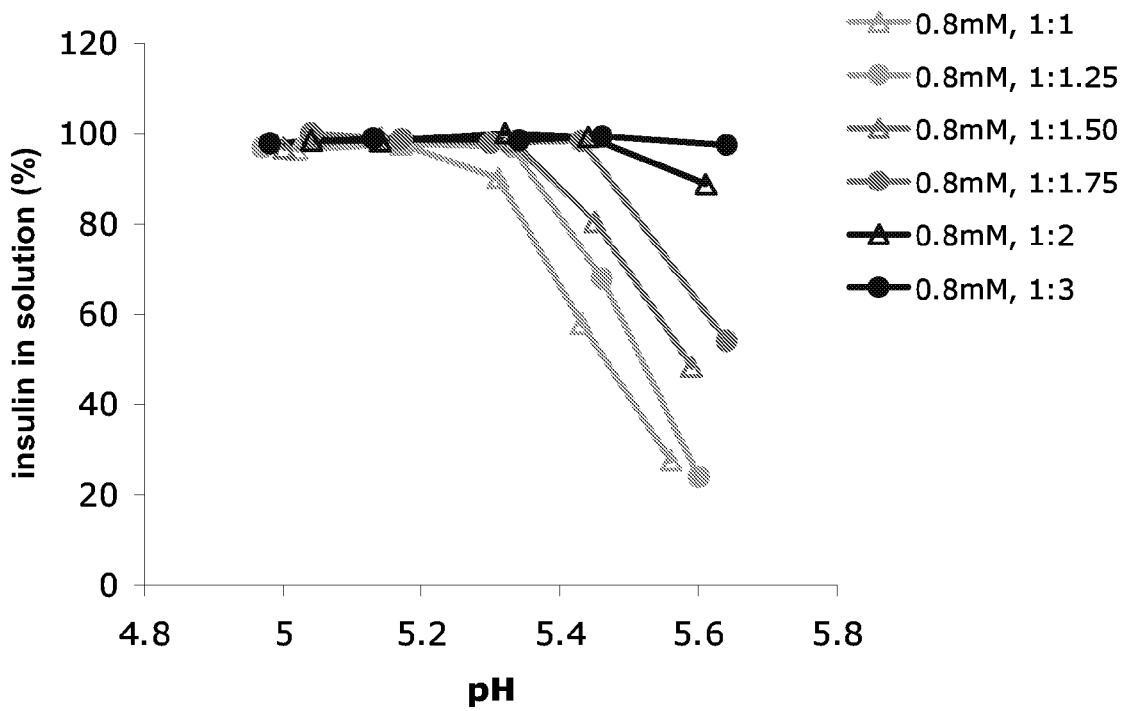
Figure 23:
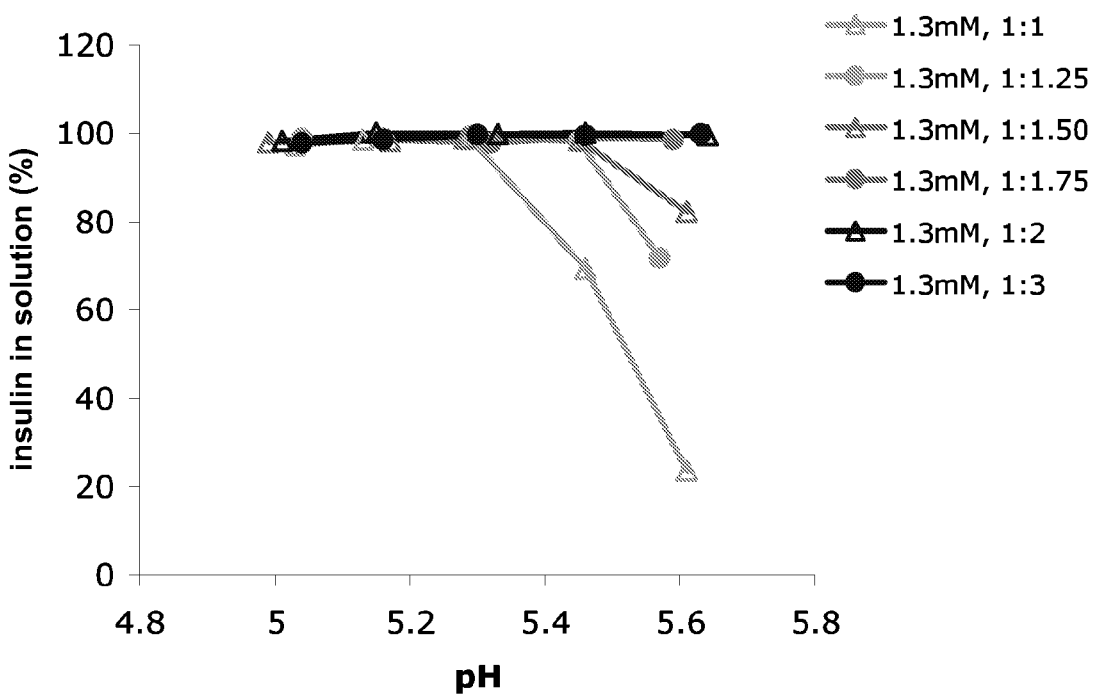

Testing the Solubility vs. pH of 0.4/0.8/1.3 mM Human Insulin in the Presence of Varying Concentrations of Protamine Acetate FIGS. 21-23 show the solubility of human insulin at three different concentrations in the presence of varying concentrations of protamine acetate. The solubility is measured after incubation of samples for 14 days at 37° C.

Compositions of preparations in FIG. 21-23 are 0.4-0.8-1.3 mM human insulin, 25 mM m-cresol, 1.6% glycerol, 40 ppm TWEEN® 20 with ratio of human insulin to protamine acetate concentrations as designated.

The data demonstrates that the relative concentration of protamine acetate to human insulin needed to solubilize human insulin in the pH-range between ~4.5 and ~6.0 depends on the absolute concentration of human insulin.

Example 12

Figure 24:
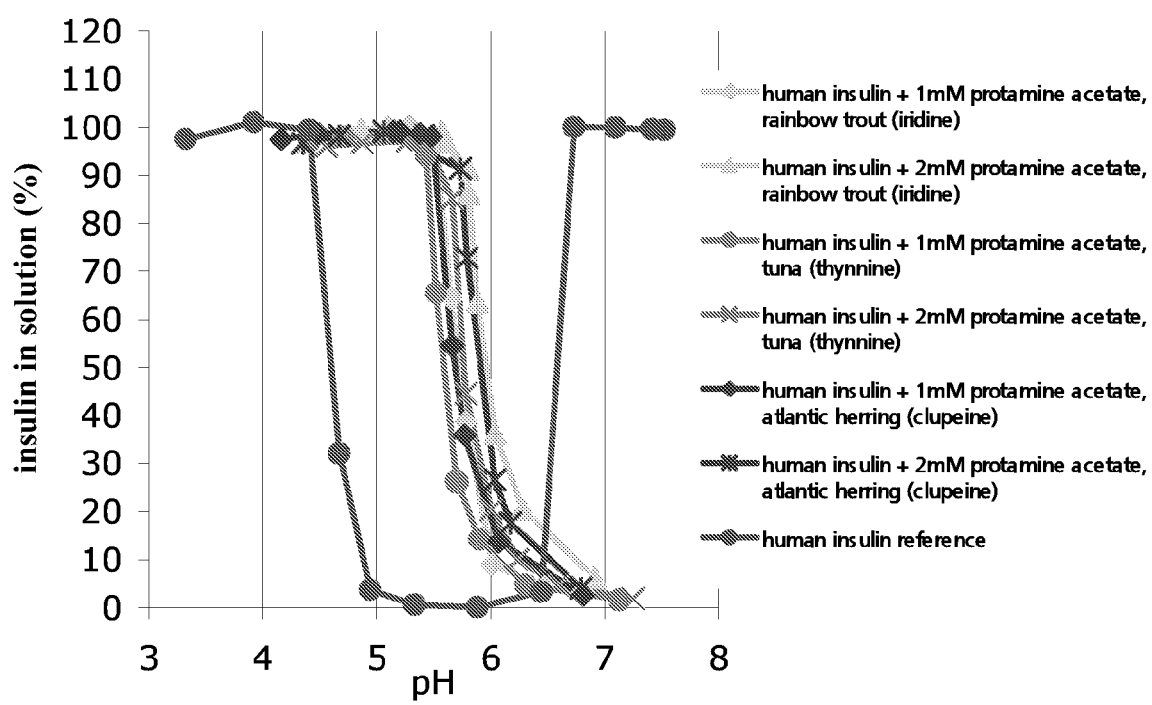
FIG. 24 show the solubility of human insulin in the presence of 1.0 mM and 2.0 mM concentrations of the acetate salt of protamine from three different species, rainbow trout (iridine), tuna (thynnine) and atlantic herring (clupeine). The protamine salts used in FIGS. 1-23 are all obtained from salmon.

Testing the Solubility vs. pH of Human Insulin in the Presence of Protamine Acetate from Different Species FIG. 24 show the solubility of human insulin in the presence of 1.0 mM and 2.0 mM concentrations of the acetate salt of protamine from three different species.

Compositions of preparations in FIG. 24 are 0.6 mM human insulin, 25 mM m-cresol, 1.6% glycerol with protamine acetate concentrations 1.0 mM and 2.0 mM. Human insulin reference is 0.6 mM human insulin, 0.3 mM $Zn^{2+}$, 30 mM phenol.

The data demonstrates that besides the acetate salt of protamine derived from salmon also the acetate salt of protamine derived from rainbow trout (iridine), tuna (thynnine) and atlantic herring (clupeine) solubilizes human insulin in the pH-range between ~4.5 and ~6.0.

EXEMPLARY EMBODIMENTS AND NON-LIMITING DESCRIPTION OF CERTAIN ASPECTS OF THE PRESENT INVENTION

Embodiment 1

A pharmaceutical formulation which is a solution comprising an insulin, an insulin analog or an insulin derivative or a mixture thereof and a protamine salt, wherein said protamine salt is present in said formulation in a concentration of greater than 0.25 mM and wherein said formulation has a pH of less than about 7.0.

Embodiment 2

The formulation according to embodiment 1, wherein the molar ratio of protamine salt to insulin is from about 0.5 to about 100.

Embodiment 3

The formulation according to embodiment 1, wherein the molar ratio of protamine salt to insulin is from about 0.5 to about 10.

Embodiment 4

The formulation according to embodiment 1, wherein the molar ratio of protamine salt to insulin is from about 0.5 to 5.

Embodiment 5

The formulation according to embodiment 1, wherein the pH of said formulation is from about 4.0 to about 7.

Embodiment 6

The formulation according to embodiment 1, wherein the pH of said formulation is from about 4.0 to about 6.5.

Embodiment 7

The formulation according to embodiment 1, wherein the pH of said formulation is from about 4.5 to about 6.0.

Embodiment 8

The formulation according to embodiment 1, further comprising a preservative.

Embodiment 9

The formulation according to embodiment 1, further comprising an isotonicity agent.

Embodiment 10

The formulation according to embodiment 1, further comprising a divalent metal ion.

Embodiment 11

The formulation according to embodiment 10, wherein the divalent metal ion is zinc.

Embodiment 12

The formulation according to embodiment 1, further comprising a surfactant.

Embodiment 13

The formulation according to embodiment 1, wherein said insulin is human insulin.

Embodiment 14

The formulation according to embodiment 1, wherein said insulin is a human insulin analog.

Embodiment 15

The formulation according to embodiment 1, wherein said insulin is a human insulin derivative.

Embodiment 16

A method of treating type 1 or type 2 diabetes, said method comprising administering to a patient in need of such treatment an effective amount of a formulation according to embodiment 1.

Embodiment 17

The formulation according to embodiment 1, wherein the protamine salt is selected from the group consisting of propionate, lactate, formiate, nitrate and acetate salts of protamine.

Embodiment 18

The formulation according to embodiment 17, wherein the protamine salt is protamine acetate.

Embodiment 19

The formulation according to embodiment 17, wherein the insulin is human insulin.

Embodiment 20

The formulation according to embodiment 17, further comprising a divalent metal ion.

Embodiment 21

The formulation according to embodiment 17, further comprising a preservative.

Embodiment 22

The formulation according to embodiment 17, further comprising an isotonicity agent.

Embodiment 23

The formulation according to embodiment 17, further comprising a surfactant.

Embodiment 24

The formulation according to embodiment 1, wherein said formulation is soluble at a pH of less than about 7.0

Embodiment 25

A method of treating type 1 or type 2 diabetes, said method comprising administering to a patient in need of such treatment an effective amount of a formulation according to embodiment 17.

Embodiment 26

The use of a formulation according to any of the embodiments 1-15, 17-24 for the preparation of a formulation for treating type 1 or type 2 diabetes.

The invention claimed is:

1. A pharmaceutical formulation which is a solution comprising an insulin, an insulin analog or an insulin derivative or a mixture thereof and a protamine salt, wherein said protamine salt is selected from the group consisting of propionate, lactate, formiate, nitrate and acetate salts of protamine, and is present in said formulation in a concentration of greater than 0.25 mM and wherein said formulation has a pH of about 4.5-6.0.

2. The formulation according to claim 1, wherein the molar ratio of protamine salt to insulin is from about 0.5 to about 100.

3. The formulation according to claim 2, wherein the molar ratio of protamine salt to insulin is from about 0.5 to about 10.

4. The formulation according to claim 3, wherein the molar ratio of protamine salt to insulin is from about 0.5 to 5.

5. The formulation according to claim 1, further comprising a preservative.

6. The formulation according to claim 5, wherein the preservative is m-cresol.

7. The formulation according to claim 1, further comprising an isotonicity agent.

8. The formulation according to claim 7, wherein the isotonicity agent is glycerol.

9. The formulation according to claim 1, further comprising a divalent metal ion.

10. The formulation according to claim 9, wherein the divalent metal ion is zinc.

11. The formulation according to claim 1, further comprising a surfactant.

12. The formulation according to claim 11, wherein the surfactant is TWEEN® 20.

13. The formulation according to claim 1, wherein said insulin is human insulin.

14. The formulation according to claim 1, wherein said insulin is a human insulin analog.

15. The formulation according to claim 1, wherein said insulin is a human insulin derivative.

16. The formulation according to claim 1, wherein the protamine salt is protamine acetate.

17. The formulation according to claim 1, wherein said formulation is soluble at a pH of 6.0 or less.

18. A method of treating type 1 or type 2 diabetes, said method comprising administering to a patient in need of such treatment an effective amount of a formulation according to claim 1.

* * * * *